(12) United States Patent
Gunderson

(10) Patent No.: US 7,783,354 B2
(45) Date of Patent: *Aug. 24, 2010

(54) METHOD AND APPARATUS FOR IDENTIFYING CARDIAC AND NON-CARDIAC OVERSENSING USING INTRACARDIAC ELECTROGRAMS

(75) Inventor: Bruce D. Gunderson, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 1792 days.

This patent is subject to a terminal disclaimer.

(21) Appl. No.: 10/418,857

(22) Filed: Apr. 18, 2003

(65) Prior Publication Data

US 2004/0015197 A1    Jan. 22, 2004

Related U.S. Application Data

(63) Continuation-in-part of application No. 10/135,080, filed on Apr. 29, 2002, now Pat. No. 7,283,863.

(51) Int. Cl.
A61N 1/00 (2006.01)
(52) U.S. Cl. .................................................. 607/27
(58) Field of Classification Search ............... 600/509, 600/510; 607/27
See application file for complete search history.

(56) References Cited

U.S. PATENT DOCUMENTS

| 4,374,382 A | 2/1983 | Markowitz |
| 5,117,824 A | 6/1992 | Keimel et al. |
| 5,158,078 A * | 10/1992 | Bennett et al. .............. 607/27 |
| 5,176,138 A * | 1/1993 | Thacker ..................... 607/22 |
| 5,193,535 A | 3/1993 | Bardy et al. |
| 5,193,550 A | 3/1993 | Duffin |
| 5,365,932 A | 11/1994 | Greenhut ................... 128/696 |
| 5,374,282 A | 12/1994 | Nichols et al. ............... 607/18 |
| 5,545,186 A | 8/1996 | Olson et al. |
| 5,564,430 A | 10/1996 | Jacobson et al. |
| 5,685,315 A | 11/1997 | McClure et al. |
| 5,776,168 A | 7/1998 | Gunderson |
| 5,891,171 A | 4/1999 | Wickham |
| 6,067,473 A | 5/2000 | Greeninger et al. |
| 6,112,119 A | 8/2000 | Schuelke et al. |
| 6,129,745 A * | 10/2000 | Sun et al. .................... 607/27 |
| 6,418,343 B1 | 7/2002 | Zhang et al. |
| 6,477,406 B1 * | 11/2002 | Turcott ..................... 600/518 |

(Continued)

FOREIGN PATENT DOCUMENTS

WO    WO 03/092810 A2    11/2003

*Primary Examiner*—Mark W Bockelman
(74) *Attorney, Agent, or Firm*—Michael J. Ostrom; Stephen W. Bauer

(57) ABSTRACT

A method and apparatus for automatically identifying various types of cardiac and non-cardiac oversensing and automatically performing a corrective action to reduce the likelihood of oversensing is provided. EGM data, including time intervals between sensed and paced events and signal morphologies, are analyzed for patterns indicative of various types of oversensing, including oversensing of far-field R-waves, R-waves, T-waves, or noise associated with electromagnetic interference, non-cardiac myopotentials, a lead fracture, or a poor lead connection. Identification of oversensing and its suspected cause are reported so that corrective action may be taken. The corrective action may include, for example, adjusting sensing parameters such as blanking periods, decay constants, decay delays, threshold values, sensitivity values, electrode configurations and the like.

32 Claims, 12 Drawing Sheets

U.S. PATENT DOCUMENTS

| | | |
|---|---|---|
| 6,539,259 B1 | 3/2003 | Weinberg et al. |
| 6,862,476 B2 * | 3/2005 | Mouchawar et al. .......... 607/27 |
| 2001/0031997 A1 | 10/2001 | Lee |
| 2001/0037366 A1 | 11/2001 | Webb et al. |
| 2003/0097157 A1 | 5/2003 | Wohlgemuth et al. |
| 2003/0204215 A1 | 10/2003 | Gunderson et al. ............ 607/27 |

* cited by examiner

METHOD AND APPARATUS FOR IDENTIFYING CARDIAC AND NON-CARDIAC OVERSENSING USING INTRACARDIAC ELECTROGRAMS

This application is a continuation-in-part (CIP) of U.S. patent application Ser. No. 10/135,080, filed Apr. 29, 2002, now U.S. Pat. No. 7,283,863 the entire content of which is incorporated herein by reference.

TECHNICAL FIELD

The present invention relates to a method and apparatus for automatically identifying cardiac and non-cardiac oversensing by an implantable cardiac device using intracardiac electrogram signals.

BACKGROUND

Implantable medical devices are available to provide therapies for restoring normal cardiac rhythms by delivering electrical shock therapy for cardioverting or defibrillating the heart in addition to cardiac pacing. Such a device, commonly known as an implantable cardioverter defibrillator or "ICD", senses a patient's heart rhythm and classifies the rhythm according to a number of rate zones in order to detect episodes of tachycardia or fibrillation. Single chamber devices are available for treating either atrial arrhythmias or ventricular arrhythmias, and dual chamber devices are available for treating both atrial and ventricular arrhythmias. Rate zone classifications may include slow tachycardia, fast tachycardia, and fibrillation.

Upon detecting an abnormal rhythm, the ICD delivers an appropriate therapy. Cardiac pacing is delivered in response to the absence of sensed intinsic depolarizations, referred to as P-waves in the atrium and R-waves in the ventricle. In response to tachycardia detection, a number of tiered therapies may be delivered beginning with anti-tachycardia pacing therapies and escalating to more aggressive shock therapies until the tachycardia is terminated. Termination of a tachycardia is commonly referred to as "cardioversion." Ventricular fibrillation (VF) is a serious life-threatening condition and is normally treated by immediately delivering high-energy shock therapy. Termination of VF is normally referred to as "defibrillation."

In modern implantable cardioverter defibrillators, the physician programs the particular anti-arrhythmia therapies into the device ahead of time, and a menu of therapies is typically provided. For example, on initial detection of an atrial or ventricular tachycardia, an anti-tachycardia pacing therapy may be selected and delivered to the chamber in which the tachycardia is diagnosed or to both chambers. On redetection of tachycardia, a more aggressive anti-tachycardia pacing therapy may be scheduled. If repeated attempts at anti-tachycardia pacing therapies fail, a higher energy cardioversion pulse may be selected. For an overview of tachycardia detection and treatment therapies reference is made to U.S. Pat. No. 5,545,186 issued to Olson et al.

Detection of tachycardia or fibrillation may also trigger the storage of the sensed intracardiac electrogram (EGM) for a period of several seconds such that the EGM signals leading up to and during a detected arrhythmia episode are available for downloading and displaying on an external programmer or other device for analysis by a physician. Such analysis aids the physician in monitoring the status of the patient and the patient's response to delivered therapies. Occasionally, cardioversion or defibrillation therapies are delivered when the patient does not feel symptomatic. In such cases, the ICD may inappropriately detect a tachycardia or fibrillation episode that does not exist and deliver an anti-arrhythmia therapy when it is not needed. Inappropriate arrhythmia detections may cause a patient to experience painful, repeated shocks within a short period of time. Anti-tachycardia pacing therapies delivered during normal sinus rhythm can potentially induce an arrhythmia in some patients. For these reasons, the delivery of a therapy in response to inappropriate arrhythmia detection is highly undesirable.

Inappropriate arrhythmia detection is generally caused by oversensing. Oversensing can be defined as the sensing of events other than the one P-wave and/or the one R-wave occurring during each normal sinus cardiac cycle. Oversensing of both cardiac and non-cardiac events can result in inappropriate arrhythmia detection by the ICD if the detected rate due to oversensing falls into an arrhythmia detection zone. Cardiac oversensing refers to oversensing of cardiac events such as far-field R-waves, T-waves, or R-waves that are sensed twice and are therefore "double-counted". Examples of cardiac oversensing are illustrated in FIG. 1. A conventional ECG signal is illustrated showing a normal cardiac cycle indicated by a P-wave, R-wave, and T-wave. Beneath the ECG, is a typical ventricular intracardiac electrogram signal (VEGM) in which a ventricular signal spike coincides with the R-wave on the ECG. During normal sensing, shown beneath the VEGM, one atrial sensed event (AS) and one ventricular sensed event (VS) occur for each cardiac cycle, corresponding to the atrial P-wave and the ventricular R-wave, respectively.

Far-field R-wave oversensing is illustrated in FIG. 1 in which one atrial sensed event (AS) per cardiac cycle corresponds to the normal P-wave and a second atrial sensed event (AS) per cardiac cycle corresponds to the R-wave. Far-field R-waves are sometimes sensed in the atria because the amplitude of an R-wave, as sensed at the atrial sensing electrodes, can reach the atrial sensitivity threshold. Therefore an atrial sensitivity setting required for sensing P-waves may also result in sensing of far-field R-waves from the ventricles.

T-wave oversensing is illustrated in FIG. 1 in which two ventricular sensed events (VS) occur during each cardiac cycle, one coinciding with the R-wave and one coinciding with the T-wave. T-wave oversensing occurs when the ventricular sensitivity setting is too sensitive, resulting in sensing of both R-waves and T-waves. T-wave oversensing also occurs when the R-wave amplitude has reduced to a point that causes the auto-adjusting threshold, which is a function of the R-wave, to decrease below the T-wave threshold. R-wave oversensing, also referred to as "R-wave double-counting," is also illustrated in FIG. 1 in which two ventricular sense events (VS) correspond to one R-wave. This "double-counting" of R-waves can occur, for example, when an R-wave complex is widened due to conditions such as bundle branch block or wide complex ventricular tachycardia. For each of these types of cardiac oversensing, generally one extra atrial or ventricular sensed event occurs per cardiac cycle, as seen in the illustrations of FIG. 1.

Non-cardiac oversensing refers to undesired sensing of other electrical signals by an ICD that are not cardiac in origin. Such non-cardiac signals are generally referred to as "noise." Noise may occur in the form of myopotentials from surrounding muscle tissue or as the result of electromagnetic interference (EMI) external to the patient. Noise may also occur when the insulation of a lead fails, a lead conductor becomes fractured, or when a lead is poorly connected to the ICD.

Examples of non-cardiac oversensing are illustrated in FIGS. 2A through 2C. In FIG. 2A, a ventricular EGM (VEGM) signal is shown with a corresponding illustration of EMI oversensing. EMI appears as relatively continuous high frequency noise on the VEGM and can be repeatedly sensed as a ventricular event (VS) by the ICD. In FIG. 2B, a ventricular EGM (VEGM) is shown with a corresponding illustration of myopotential oversensing. Myopotentials may appear as lower frequency noise on the VEGM than EMI, resulting in somewhat less frequent but repeated ventricular sensed events (VS). In FIG. 2C, a ventricular EGM (VEGM) is shown corresponding to noise associated with a lead fracture or a poor lead connection. This type of noise can result in saturation of the sense amplifiers and intermittent bursts of noise. Oversensing due to a lead fracture or poor lead connection, therefore, produces intermittent clusters of ventricular sensed events (VS), as shown in FIG. 2C. As seen in FIGS. 2A through 2C, non-cardiac oversensing is generally associated with multiple oversensed events per cardiac cycle that may be intermittent or continuous, of high or low amplitude, and of relatively low or high frequency.

Since these problems of oversensing can be rare and are therefore not routinely encountered in all patients, the task of recognizing and trouble-shooting oversensing can be a challenging one to the physician. Oversensing may not be recognized until inappropriate arrhythmia detections are made and unneeded therapies are delivered. While stored EGM data can be useful in identifying and trouble-shooting inappropriate arrhythmia detections due to oversensing, valid arrhythmia detections may occur the majority of the time with only an occasional inappropriate detection occurring, making the identification of EGM episodes associated with inappropriate detections a time-consuming task. Once an inappropriate detection is identified, the numerous types of oversensing that may have caused the detection make diagnosing the problem complex. With a growing number of ICD patients in broad geographical distributions, clinicians need to be able to quickly and confidently diagnose and correct such problems. What is needed, therefore, is an automated method for recognizing oversensing and specifically identifying the type of oversensing present so that a physician may make prompt corrective actions with confidence.

SUMMARY

The present invention addresses the problem of oversensing in an implantable cardiac stimulation device and the associated difficulties in trouble-shooting oversensing problems. Further, the invention is directed to automatically performing corrective actions upon detection of oversensing to reduce the likelihood of future oversensing. As will be described, the corrective actions are dynamically performed to reduce the likelihood of future oversensing. Aspects of the present invention include a method for automatically evaluating EGM data for determining if oversensing is present and, if so, determining the most likely cause of oversensing. Further aspects of the present invention allow inappropriate arrhythmia detection due to oversensing to be identified. Still further aspects of the present invention include generating a report of an oversensing problem and recommending or automatically taking a corrective action to eliminate oversensing. For example, the implanted device may adjust one or more sensing parameters including blanking periods, decay constants, decay delays, threshold values, sensitivity values, electrode configurations and the like as corrective action to eliminate oversensing. In some embodiments, the implanted medical device adjusts the sensing parameters iteratively and incrementally a number of times.

Methods included in the present invention may be implemented in an external device, such as a programmer or personal computer, for offline processing of EGM data that has been stored in an implanted ICD and uplinked to an external device. The present invention may also be implemented in an implantable monitor, ICD or pacemaker for either post-processing or real-time processing of EGM data.

In operation, an algorithm is executed for analyzing EGM data, including time intervals between sensed and/or paced events and sensed signal morphologies. This analysis searches for sensed interval patterns that are indicative of specific types of oversensing, including both cardiac and non-cardiac types of oversensing. Near-field and/or far-field sensed EGM data may be analyzed. The analysis may also include examination of signal morphology using template matching to verify specific types of oversensing. Various types of cardiac oversensing that may be identified include, but are not limited to, far-field R-wave oversensing, R-wave oversensing, and T-wave oversensing. Non-cardiac causes of oversensing that may be diagnosed include electromagnetic interference, non-cardiac myopotentials, a lead fracture, or a poor lead connection.

When methods included in the present invention for recognizing oversensing are implemented in an external device, EGM data that has been stored in an implanted device in response to an arrhythmia detection or other monitoring algorithm may be uplinked to the external device. The EGM data is analyzed, and, if oversensing is identified, a report is generated to notify a physician of the incidence of oversensing and its likely cause. The report may optionally recommend a corrective action for eliminating the oversensing based on the type of oversensing detected.

When methods included in the present invention are implemented in an implantable device, such as an ICD or pacemaker, the EGM analysis may be performed in response to a triggered storage of an EGM episode or on a periodic basis to detect oversensing. Recognition of an oversensing problem may trigger any of a number of responsive actions. A warning flag may be generated to alert a physician of an oversensing problem the next time a device interrogation is performed. A patient notification signal may be generated to notify the patient to seek medical attention for correcting the oversensing problem. A corrective action, e.g., modification of one or more sensing parameters, may be taken automatically by the implanted device to eliminate oversensing, such as automatically adjusting an atrial or ventricular sensitivity setting or changing a sensing electrode configuration. The implanted device dynamically performs the automatic corrective action, i.e., the implanted device operates in accordance with originally programmed sensing parameters for a plurality of cardiac cycles, and upon detecting oversensing, the implanted device automatically provides the corrective action to avoid future oversensing. Thus, the implanted device performs the corrective action "on the fly" whenever oversensing is detected. The implanted device may further use previously stored cardiac episode data to determine whether the adjusted sensing parameters will properly detect true cardiac episodes. For example, the implanted device may apply the adjusted sensing parameters to a previously stored intracardiac electrogram of a previous ventricular fibrillation (VF) episode to determine whether, given the adjusted sensing parameters, the implanted device is able to correctly identify the VF episode. When the adjusted parameters result in the inability to accurately detect the cardiac episode, the implanted device resets the adjusted parameters to their original settings.

EGM analysis may also be performed in real-time when methods and apparatus included in the present invention are incorporated in an implantable device. The diagnosis of oversensing in real time may trigger storage of EGM data as well as generate a warning flag and/or a patient notification signal. A corrective action may also be automatically taken by the implanted device in order to eliminate the oversensing. For example, the implanted device may modify one or more sensing parameters including blanking periods, decay constants, decay delays, threshold values, sensitivity values, electrode configurations and the like. As described, the modifications made to the sensing parameters by implanted medical device can be incremental and iterative. In an ICD, recognition of oversensing allows identification of inappropriate arrhythmia detections due to oversensing. If arrhythmia detection is determined to be inappropriate, a scheduled anti-arrhythmia therapy may optionally be withheld. Alternatively, the arrhythmia therapy may still be delivered but with a patient notification signal so that the patient will seek medical attention to correct the oversensing problem.

Aspects of the present invention, which allow automatic identification of oversensing, can save a physician considerable time and, moreover, prevent inappropriate arrhythmia detections from going unnoticed. Once oversensing is identified and its probable cause diagnosed, prompt corrective action may be taken so that accurate sensing of heart rhythms may be achieved and appropriate stimulation therapies delivered only as needed. Repeated delivery of unnecessary cardioversion or defibrillation therapies in response to inappropriate arrhythmia detections due to oversensing may be avoided. The methods included in the present invention may advantageously be implemented in a central computer system, a network or web-based system, allowing a physician to remotely diagnose an oversensing problem. Alternatively, the methods and apparatus included in the present invention may be implemented in an implanted device so that corrective action may be performed automatically to eliminate oversensing.

In one embodiment, the invention provides a method comprising operating an implanted medical device in accordance with sensing parameters for a plurality of cardiac cycles, identifying oversensing by the implanted medical device, and automatically adjusting at least one of the sensing parameters of the implanted medical device in response to identifying the oversensing.

In another embodiment, the invention provides a computer-readable medium comprising instructions to cause a processor to operate an implanted medical device in accordance with sensing parameters for a plurality of cardiac cycles, identify oversensing by the implanted medical device, and automatically adjust at least one sensing parameter of the implanted medical device in response to identifying the oversensing.

In a further embodiment, the invention provides an implantable medical device comprising at least one sensing electrode to sense cardiac data from a heart of a patient in accordance with programmed sensing parameters for a plurality of cardiac cycles and a processor to identify oversensing by the implanted medical device based on the sensed cardiac data and automatically adjust at least one of the sensing parameter of the implanted medical device in response to identifying the oversensing.

In another embodiment, the invention provides an implantable medical device comprising means for operating an implantable medical device in accordance with sensing parameters for a plurality of cardiac cycles, means for identifying oversensing by the implantable medical device, and means for automatically performing a corrective action to reduce the likelihood of oversensing.

The details of one or more embodiments of the invention are set forth in the accompanying drawings and the description below. Other features and inventive aspects of the invention will be apparent from the description and drawings, and from the claims.

DETAILED DESCRIPTION

The present invention is aimed at providing a system and method for automatically identifying and trouble-shooting cardiac and/or non-cardiac oversensing by an implantable cardiac stimulation device. The methods included in the present invention may be used in conjunction with, or incorporated in, an implantable cardiac stimulation device such as a pacemaker or an implantable cardioverter defibrillator (ICD), or other monitoring devices, capable of storing sensed intracardiac electrogram (EGM) data.

Figure 3:
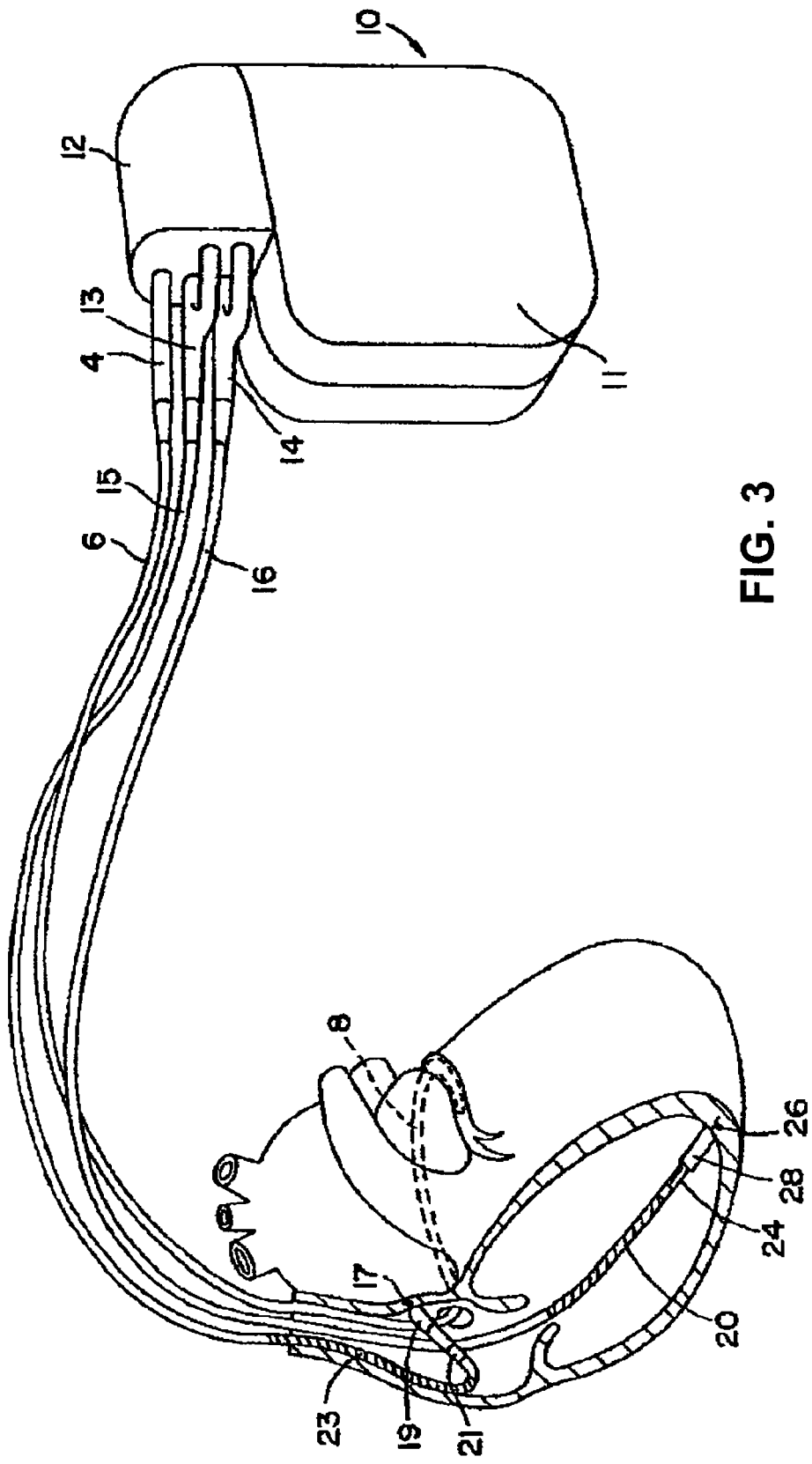
FIG. 3 is an illustration of an implantable cardiac stimulation device capable of pacemaking, cardioversion, and defibrillation in communication with a patient's heart via three stimulation and sensing leads.

An exemplary ICD 10 is shown in FIG. 3, with which methods included in the present invention may be used. In accordance with the invention, ICD 10 identifies oversensing and automatically provides a corrective action, e.g., adjusts one or more sensing parameters or electrode configurations to avoid future oversensing. Particularly, ICD 10 operates in accordance with originally programmed sensing parameters for a plurality of cardiac cycles, and upon detecting oversensing, automatically provides the corrective action to avoid future oversensing. In this manner, the corrective actions provided by ICD 10 to avoid future oversensing are dynamically performed.

The ICD 10 is shown coupled to a heart of a patient by way of three leads 6, 15, and 16. A connector block 12 receives the proximal end of a right ventricular lead 16, a right atrial lead 15 and a coronary sinus lead 6, used for positioning electrodes for sensing and stimulation in three or four heart chambers. In FIG. 3, right ventricular lead 16 is positioned such that its distal end is in the right ventricle for sensing right ventricular cardiac signals and delivering pacing or shocking pulses in the right ventricle. For these purposes, right ventricular lead 16 is equipped with a ring electrode 24, an extendable helix electrode 26 mounted retractably within an electrode head 28, and a coil electrode 20, each of which are connected to an insulated conductor within the body of lead 16. The proximal end of the insulated conductors are coupled to corresponding connectors carried by bifurcated connector 14 at the proximal end of lead 16 for providing electrical connection to the ICD 10.

The right atrial lead 15 is positioned such that its distal end is in the vicinity of the right atrium and the superior vena cava. Lead 15 is equipped with a ring electrode 21 and an extendable helix electrode 17, mounted retractably within electrode head 19, for sensing and pacing in the right atrium. Lead 15 is further equipped with a coil electrode 23 for delivering high-energy shock therapy. The ring electrode 21, the helix electrode 17 and the coil electrode 23 are each connected to an insulated conductor with the body of the right atrial lead 15. Each insulated conductor is coupled at its proximal end to a connector carried by bifurcated connector 13.

The coronary sinus lead 6 is advanced within the vasculature of the left side of the heart via the coronary sinus and great cardiac vein. The coronary sinus lead 6 is shown in the embodiment of FIG. 3 as having a defibrillation coil electrode 8 that may be used in combination with either the coil electrode 20 or the coil electrode 23 for delivering electrical shocks for cardioversion and defibrillation therapies. In other embodiments, coronary sinus lead 6 may also be equipped with a distal tip electrode and ring electrode for pacing and sensing functions in the left chambers of the heart. The coil electrode 8 is coupled to an insulated conductor within the body of lead 6, which provides connection to the proximal connector 4.

The electrodes 17 and 21 or 24 and 26 may be used as true bipolar pairs, commonly referred to as a "tip-to-ring" configuration. Further, electrode 17 and coil electrode 20 or electrode 24 and coil electrode 23 may be used as integrated bipolar pairs, commonly referred to as a "tip-to-coil" configuration. In accordance with the invention, ICD 10 may, for example, adjust the electrode configuration from a tip-to-ring configuration, e.g., true bipolar sensing, to a tip-to-coil configuration, e.g., integrated bipolar sensing, upon detection of oversensing in order to reduce the likelihood of future oversensing. In other words, the electrode polarities can be reselected in response to detection of oversensing in an effort to reduce susceptibility of oversensing. In some cases, electrodes 17, 21, 24, and 26 may be used individually in a unipolar configuration with the device housing 11 serving as the indifferent electrode, commonly referred to as the "can" or "case" electrode.

The device housing 11 may also serve as a subcutaneous defibrillation electrode in combination with one or more of the defibrillation coil electrodes 8, 20 or 23 for defibrillation of the atria or ventricles. It is recognized that alternate lead systems may be substituted for the three lead system illustrated in FIG. 3. While a particular multi-chamber ICD and lead system is illustrated in FIG. 3, methodologies included in the present invention may adapted for use with any single chamber, dual chamber, or multi-chamber ICD or pacemaker system, or other cardiac monitoring device.

Figure 4:
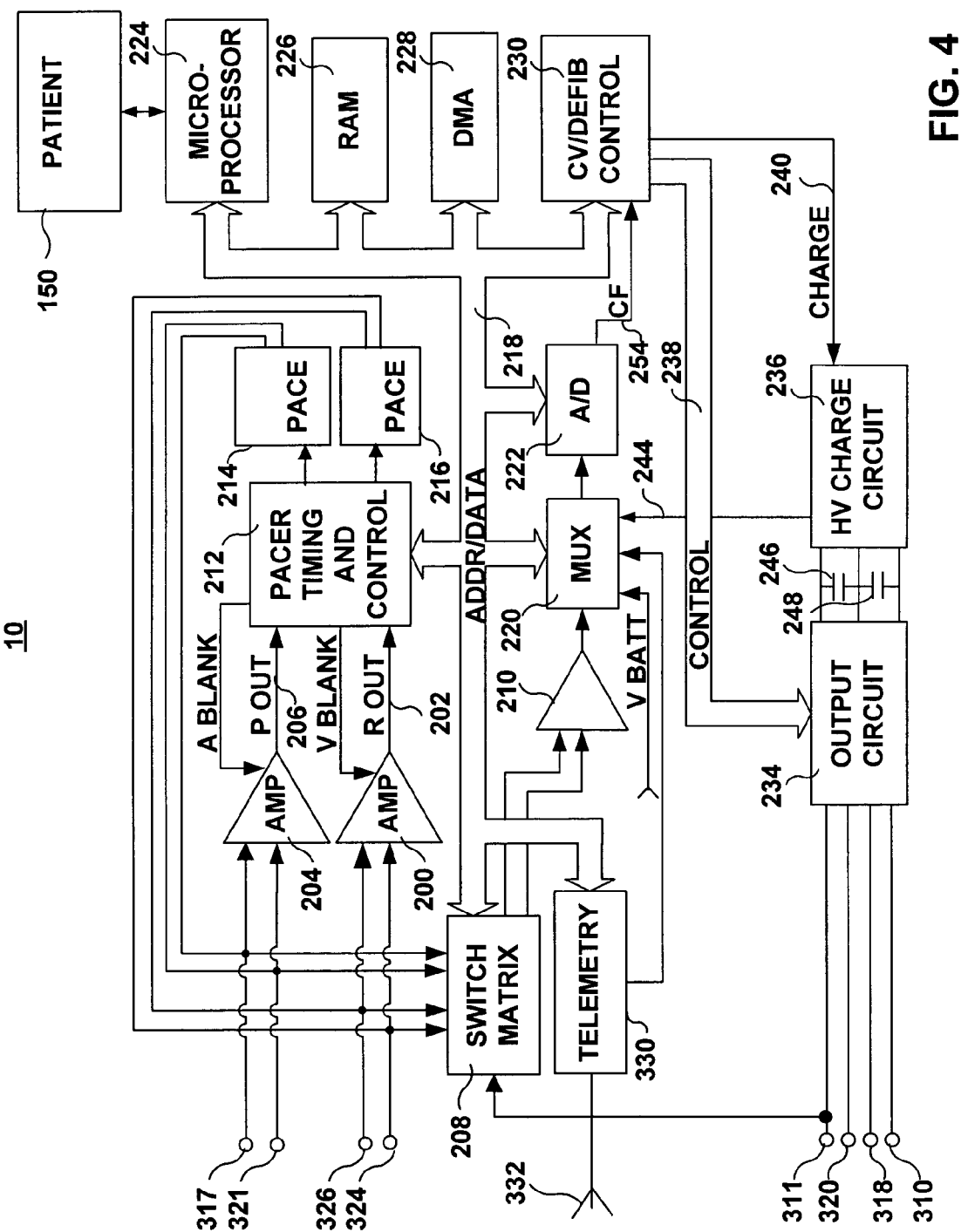
FIG. 4 is a functional, block diagram of the implantable pacemaker cardioverter defibrillator shown in FIG. 3.

A functional schematic diagram of the ICD 10 is shown in FIG. 4. This diagram should be taken as exemplary of the type of device with which the invention may be embodied and not as limiting. The disclosed embodiment shown in FIG. 4 is a microprocessor-controlled device, but the methods of the present invention may also be practiced with other types of devices such as those employing dedicated digital circuitry.

With regard to the electrode system illustrated in FIG. 3, ICD 10 is provided with a number of connection terminals for achieving electrical connection to the leads 6, 15, and 16 and their respective electrodes. A connection terminal 311 provides electrical connection to the housing 11 for use as the indifferent electrode during unipolar stimulation or sensing. The connection terminals 320, 310, and 318 provide electrical connection to coil electrodes 20, 8 and 23 respectively. Each of these connection terminals 311, 320, 310, and 318 are coupled to the high voltage output circuit 234 to facilitate the delivery of high energy shocking pulses to the heart using one or more of the coil electrodes 8, 20, and 23 and optionally the housing 11.

The connection terminals 317 and 321 provide electrical connection to the helix electrode 17 and the ring electrode 21 positioned in the right atrium. The connection terminals 317 and 321 are further coupled to an atrial sense amplifier 204 for sensing atrial signals such as P-waves. The connection terminals 326 and 324 provide electrical connection to the helix electrode 26 and the ring electrode 24 positioned in the right ventricle. The connection terminals 326 and 324 are further coupled to a ventricular sense amplifier 200 for sensing ventricular signals.

The atrial sense amplifier 204 and the ventricular sense amplifier 200 preferably take the form of automatic gain controlled amplifiers with adjustable sensitivity. In accordance with the invention, ICD 10 and, more specifically, microprocessor 224 automatically adjusts the sensitivity of atrial sense amplifier 204, ventricular sense amplifier 200 or both in response to detection of oversensing in order to reduce the likelihood of oversensing. Ventricular sense amplifier 200 and atrial sense amplifier 204 operate in accordance with originally programmed sensing parameters for a plurality of cardiac cycles, and upon detecting oversensing, automatically provides the corrective action to avoid future oversensing. In this manner, the adjustments provided by ICD 10 to amplifiers 200 and 204 to avoid future oversensing are dynamic in nature. Particularly, microprocessor 224 increases a sensitivity value of the amplifiers, thus reducing the sensitivity, when oversensing is detected. Atrial sense amplifier 204 and ventricular sense amplifier 200 receive timing information from pacer timing and control circuitry 212. Specifically, atrial sense amplifier 204 and ventricular sense amplifier 200 receive blanking period input, e.g., ABLANK and VBLANK, respectively, which indicates the amount of time the electrodes are "turned off" in order to prevent saturation due to an applied pacing pulse or defibrillation shock. As will be described, the blanking periods of atrial sense amplifier 204 and ventricular sense amplifier 200 and, in turn, the blanking periods of sensing electrodes associated with the respective amplifiers may be automatically adjusted by ICD 10 to reduce the likelihood of oversensing. The general operation of the ventricular sense amplifier 200 and the atrial sense amplifier 204 may correspond to that disclosed in U.S. Pat. No. 5,117,824, by Keimel, et al., incorporated herein by reference in its entirety. Whenever a signal received by atrial sense amplifier 204 exceeds an atrial sensitivity, a signal is generated on the P-out signal line 206. Whenever a signal received by the ventricular sense amplifier 200 exceeds a ventricular sensitivity, a signal is generated on the R-out signal line 202.

Switch matrix 208 is used to select which of the available electrodes are coupled to a wide band amplifier 210 for use in digital signal analysis. Selection of the electrodes is controlled by the microprocessor 224 via data/address bus 218. The selected electrode configuration may be varied as desired for the various sensing, pacing, cardioversion and defibrillation functions of the ICD 10. Specifically, microprocessor 224 may modify the electrode configurations based on detection of oversensing due to cardiac or non-cardiac origins. Upon detection of R-wave oversensing, for example, microprocessor 224 may modify the electrode configuration of the right ventricle from true bipolar sensing, e.g., tip-to-ring, to integrated bipolar sensing, e.g., tip-to-coil.

Signals from the electrodes selected for coupling to bandpass amplifier 210 are provided to multiplexer 220, and thereafter converted to multi-bit digital signals by A/D converter 222, for storage in random access memory 226 under control of direct memory access circuit 228. Microprocessor 224 may employ digital signal analysis techniques to characterize the digitized signals stored in random access memory 226 to recognize and classify the patient's heart rhythm employing any of the numerous signal processing methodologies known in the art. An exemplary tachyarrhythmia recognition system is described in U.S. Pat. No. 5,545,186 issued to Olson et al, incorporated herein by reference in its entirety.

Upon detection of an arrhythmia, an episode of EGM data, along with sensed intervals and corresponding annotations of sensed events, are preferably stored in random access memory 226. The EGM signals stored may be sensed from programmed near-field and/or far-field sensing electrode pairs. Typically, a near-field sensing electrode pair includes a tip electrode and a ring electrode located in the atrium or the ventricle, such as electrodes 17 and 21 or electrodes 26 and 24. A far-field sensing electrode pair includes electrodes spaced further apart such as any of: the defibrillation coil electrodes 8, 20 or 23 with housing 11; a tip electrode 17 or 26 with housing 11; a tip electrode 17 or 26 with a defibrillation coil electrode 20 or 23; or atrial tip electrode 17 with ventricular ring electrode 24. The use of near-field and far-field EGM sensing of arrhythmia episodes is described in U.S. Pat. No. 5,193,535, issued to Bardy, incorporated herein by reference in its entirety. Annotation of sensed events, which may be displayed and stored with EGM data, is described in U.S. Pat. No. 4,374,382 issued to Markowitz, incorporated herein by reference in its entirety.

The telemetry circuit 330 receives downlink telemetry from and sends uplink telemetry to an external programmer, as is conventional in implantable anti-arrhythmia devices, by means of an antenna 332. Data to be uplinked to the programmer and control signals for the telemetry circuit are provided by microprocessor 224 via address/data bus 218. EGM data that has been stored upon arrhythmia detection or as triggered by other monitoring algorithms may be uplinked to an external programmer using telemetry circuit 330. Received telemetry is provided to microprocessor 224 via multiplexer 220. Numerous types of telemetry systems known in the art for use in implantable devices may be used.

The remainder of the circuitry illustrated in FIG. 4 is an exemplary embodiment of circuitry dedicated to providing cardiac pacing, cardioversion and defibrillation therapies. The pacer timing and control circuitry 212 includes programmable digital counters which control the basic time intervals associated with various single, dual or multi-chamber pacing modes or anti-tachycardia pacing therapies delivered in the atria or ventricles. Pacer circuitry 212 also determines the amplitude of the cardiac pacing pulses under the control of microprocessor 224.

During pacing, escape interval counters within pacer timing and control circuitry 212 are reset upon sensing of R-waves or P-waves as indicated by signals on lines 202 and 206, respectively. In accordance with the selected mode of pacing, pacing pulses are generated by atrial pacer output circuit 214 and ventricular pacer output circuit 216. The pacer output circuits 214 and 216 are coupled to the desired electrodes for pacing via switch matrix 208. The escape interval counters are reset upon generation of pacing pulses, and thereby control the basic timing of cardiac pacing functions, including anti-tachycardia pacing.

The durations of the escape intervals are determined by microprocessor 224 via data/address bus 218. The value of the count present in the escape interval counters when reset by sensed R-waves or P-waves can be used to measure R-R intervals and P-P intervals for detecting the occurrence of a variety of arrhythmias.

The microprocessor 224 includes associated read-only memory (ROM) in which stored programs controlling the operation of the microprocessor 224 reside. A portion of the random access memory (RAM) 226 may be configured as a number of recirculating buffers capable of holding a series of measured intervals for analysis by the microprocessor 224 for predicting or diagnosing an arrhythmia.

In response to the detection of tachycardia, anti-tachycardia pacing therapy can be delivered by loading a regimen from microprocessor 224 into the pacer timing and control circuitry 212 according to the type of tachycardia detected. In the event that higher voltage cardioversion or defibrillation pulses are required, microprocessor 224 activates the cardioversion and defibrillation control circuitry 230 to initiate charging of the high voltage capacitors 246 and 248 via charging circuit 236 under the control of high voltage charging control line 240. The voltage on the high voltage capacitors is monitored via a voltage capacitor (VCAP) line 244, which is passed through the multiplexer 220. When the voltage reaches a predetermined value set by microprocessor 224, a logic signal is generated on the capacitor full (CF) line 254, terminating charging. The defibrillation or cardioversion pulse is delivered to the heart under the control of the pacer timing and control circuitry 212 by an output circuit 234 via a control bus 238. The output circuit 234 determines the electrodes used for delivering the cardioversion or defibrillation pulse and the pulse wave shape.

In one embodiment, the ICD 10 may be equipped with a patient notification system 150. Any patient notification method known in the art may be used such as generating perceivable twitch stimulation or an audible sound. A patient notification system may include an audio transducer that emits audible sounds including voiced statements or musical tones stored in analog memory and correlated to a programming or interrogation operating algorithm or to a warning trigger event as generally described in U.S. Pat. No. 6,067,473 issued to Greeninger et al., incorporated herein by reference in its entirety.

Figure 5:
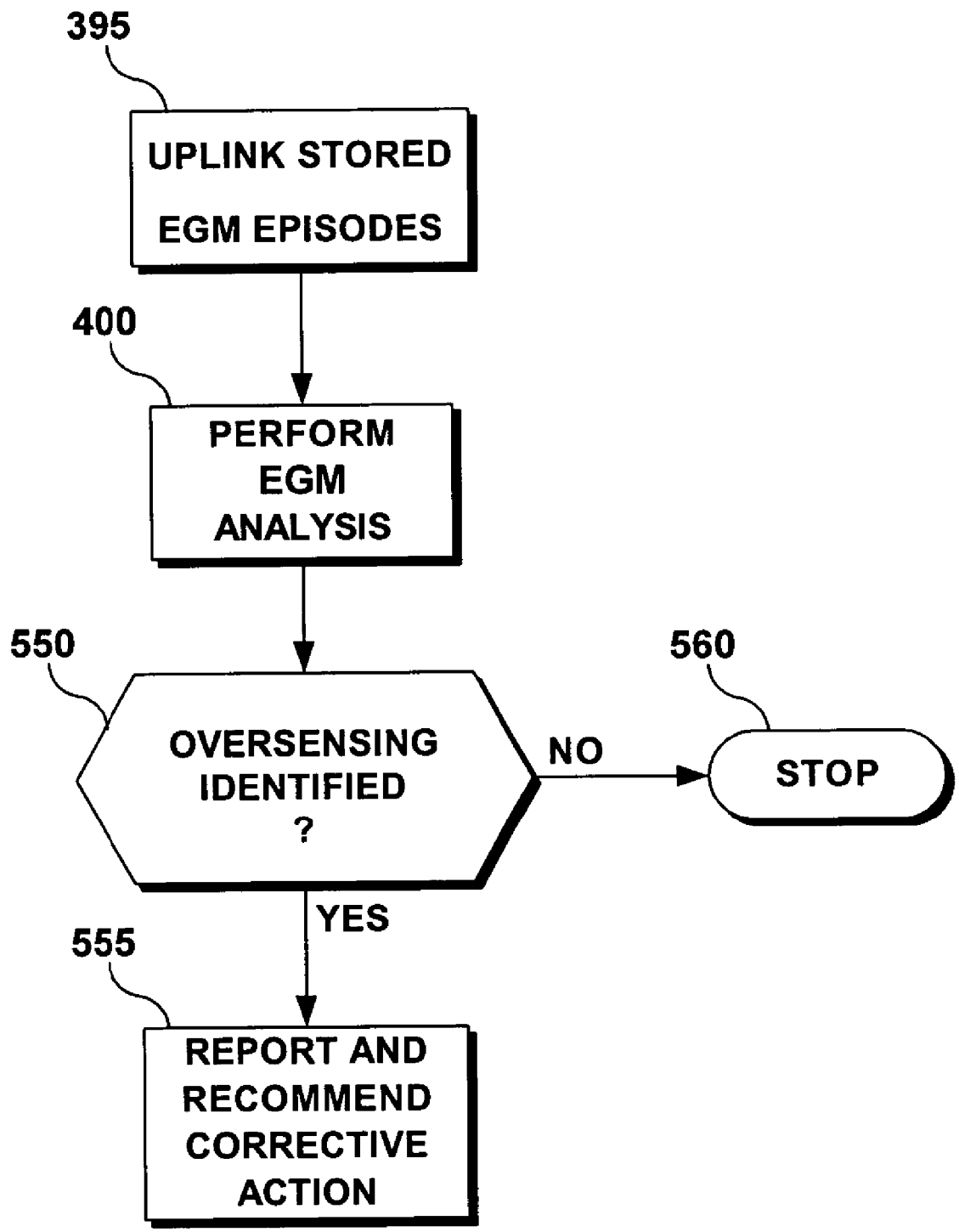
FIG. 5 is a flow chart providing an overview of one embodiment of the present invention for automatically identifying oversensing from EGM data stored in the ICD shown in FIG. 4 and uplinked to an external device.

In FIG. 5 a flow diagram is shown providing an overview of the operations included in a preferred embodiment of the present invention for identifying oversensing and diagnosing the type of oversensing that is occurring. Stored EGM data in response to arrhythmia detection may be analyzed according to the methods shown in FIG. 5 in order to identify if an arrhythmia detection is inappropriate due to oversensing. Stored EGM data triggered by other monitoring algorithms besides arrhythmia detection, such as the monitoring algorithm described in U.S. Pat. No. 5,776,168 issued to Gunderson, incorporated herein by reference in its entirety, may also be analyzed for the presence of oversensing using the methods of FIG. 5.

The operations shown in FIG. 5 are preferably implemented in an external programmer, personal computer or other external device for off-line processing of EGM data stored in an implanted device, such as the ICD 10 shown in FIG. 4. At step 395, stored EGM episodes are uplinked via telemetry circuit 330 to the external device. Stored episode data preferably includes an EGM signal, sensed and/or paced interval data and corresponding annotations of sensed and/or paced events. If the episode data is stored in response to an arrhythmia detection, EGM data leading up to and including the arrhythmia episode is stored and uplinked to the external device for analysis. Such data storage is provided in commercially available devices, for example in the Model 7275 GEM® III Dual Chamber Implantable Cardioverter Defibrillator available from Medtronic, Inc., Minneapolis, Minn.

Program code stored in memory of the external programmer or another microprocessor-controlled device is executed at step 400 to analyze the EGM episode data offline. For example, uplinked EGM data may be saved to a diskette for offline processing at a later time or may be transferred via Internet to a central computer for analysis at a remote location. Reference is made to U.S. patent application Ser. No. 20,010,031,997 entitled "Instrumentation and software for remote monitoring and programming of implantable medical devices (IMDs)" to Lee, and U.S. patent application Ser. No. 20,010,037,366 entitled "System and method for providing remote expert communications and video capabilities for use during a medical procedure" to Webb et al., both patents incorporated herein by reference in their entirety.

As will be described in detail with reference to FIGS. 7 and 8, analysis of the EGM data includes evaluation of sensed and/or paced interval patterns and signal morphology to allow incidents of cardiac or non-cardiac oversensing to be recognized. If oversensing is identified, as determined at decision step 550, a report is generated at step 555 indicating the suspected type of oversensing detected. In one embodiment, a corrective action may be recommended at step 555 based on the type of oversensing identified. A recommended corrective action may be any of: reprogramming a sensing parameter, e.g., sensitivity value, blanking period, sensing decay constant, sensing decay delay, auto-adjusting sensitivity threshold, reprogramming a sensing electrode configuration, tightening set screws in the connector block 12 of the ICD 10, investigating for a likely lead fracture that requires repair or lead replacement, or other actions aimed at eliminating oversensing. If no oversensing is identified at decision step 550, the operations shown in FIG. 5 are terminated at step 560.

The operations shown in FIG. 5 could alternatively be performed by the implanted ICD 10 as post-processing of stored EGM episode data. Program code may be stored in microprocessor 224 for analyzing stored EGM episode data, for example subsequent to an arrhythmia detection, or on a periodic basis. If oversensing is identified at decision step 550, a report may be generated at step 555 that will be uplinked to an external programmer the next time the ICD 10 is interrogated. The report may notify a physician of the date and time that an episode of oversensing was identified along with the suspected cause, such as R-wave oversensing, T-wave oversensing, P-wave oversensing, lead fracture, or otherwise. The report may further recommend a corrective action, such as reprogramming ventricular sensitivity, repair or replace a lead, or otherwise. Alternatively or additionally, a patient warning signal may be generated by patient notification circuitry 150 at the time that an oversensing episode is identified, advising the patient to seek medical attention.

Figure 6:
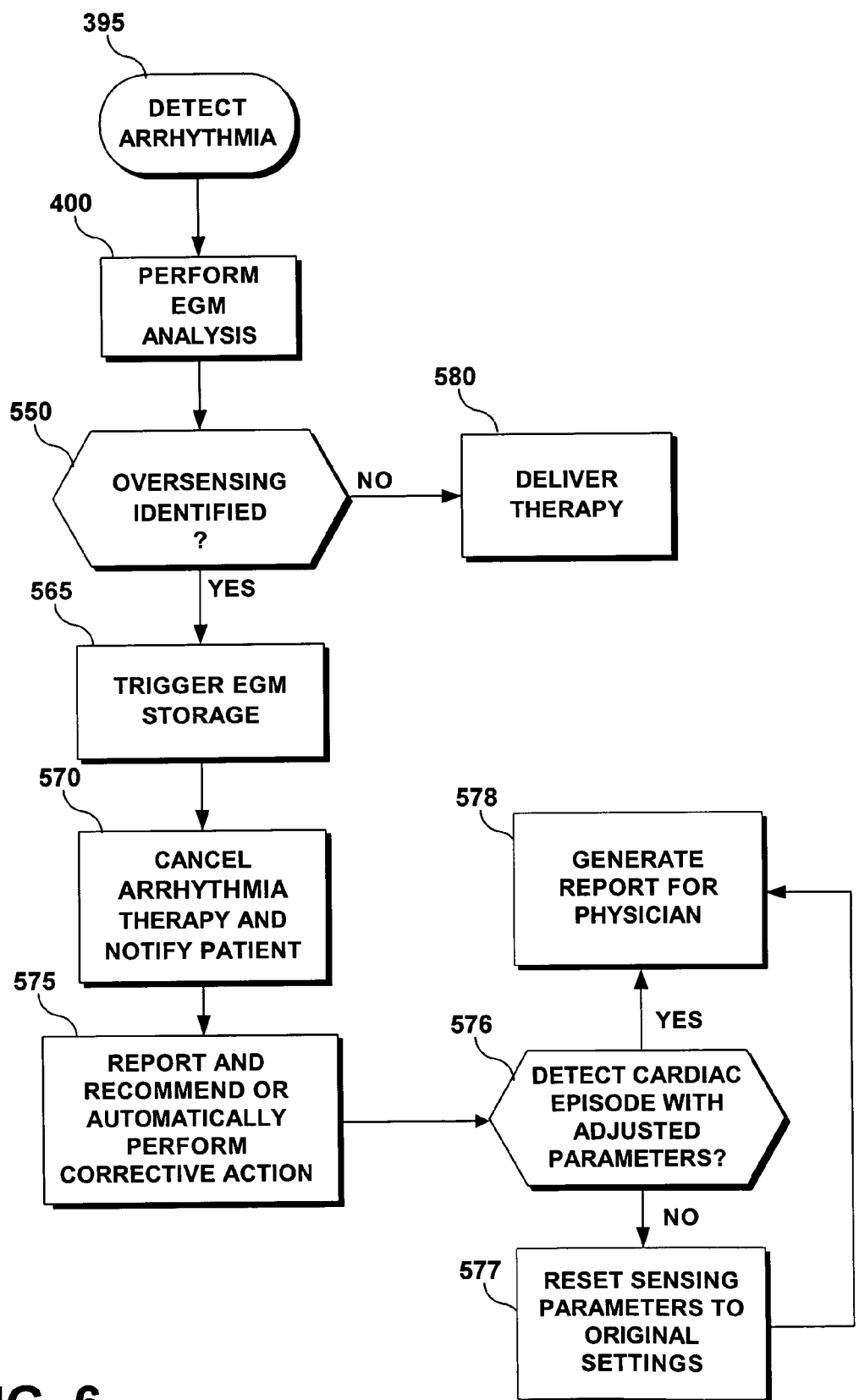
FIG. 6 is a flow chart providing an overview of another embodiment of the present invention implemented in the ICD shown in FIG. 4 for automatically identifying oversensing in real time.

In FIG. 6, a flow chart is shown providing an overview of the operations included in the present invention when it is embodied in an implantable ICD, such as ICD 10, to allow real-time EGM analysis to be performed. Real-time EGM analysis allows oversensing to be identified as it occurs, for example before a cardioversion or defibrillation therapy is delivered in response to inappropriate arrhythmia detection due to oversensing. In the embodiment shown in FIG. 6, the EGM analysis performed at step 400 is triggered by arrhythmia detection at step 395. The EGM analysis may, for example, include comparing characteristics of cardiac electrograms to determine whether the detected cardiac event is a false detection due to oversensing. Specifically, EGM analysis performed at step 400 determines the origin of oversensing, if oversensing occurred, as well as corrective actions that may be taken to prevent the likelihood of future oversensing. If the EGM analysis results in oversensing being identified at decision step 550, storage of the EGM episode including the oversensing may be triggered at step 565. The stored EGM may then be uplinked to an external device at a later time for analysis by a physician to allow verification of the detected oversensing and for determining a corrective action.

Since the detected arrhythmia is an inappropriate detection due to oversensing, any scheduled anti-arrhythmia therapy may optionally be cancelled by the ICD 10 at step 570. If a therapy is cancelled, a patient notification signal may be generated at step 570 advising the patient to seek medical attention.

Even if oversensing is identified at step 550 and a detected arrhythmia is therefore suspected to be an inappropriate detection, a scheduled arrhythmia therapy may still be delivered to ensure that a therapy is not withheld when it is actually needed. A report of the oversensing and the suspected cause, however, are generated at step 575 in the manner described previously, so that corrective action taken by a physician, or automatically by the ICD 10, may be performed to prevent future inappropriate arrhythmia detections and unneeded delivery of cardioversion or defibrillation therapies. In accordance with the invention, ICD 10 automatically performs a corrective action based on the suspected cause of oversensing at step 575 to prevent future inappropriate arrhythmia detections and unneeded delivery of cardioversion or defibrillation therapies. The automatic corrective action is dynamic, in that ICD 10 operates in accordance with originally programmed sensing parameters for a plurality of cardiac cycles, and upon detecting oversensing, ICD 10 automatically provides the corrective action to avoid future oversensing. Thus, ICD 10 performs the corrective action "on the fly" whenever oversensing is detected. The corrective action may include, for example, automatically adjusting sensing parameters, such as automatically resetting a programmed sensitivity, automatically adjusting a blanking period following delivery of a pace, automatically adjusting a programmed decay constant of a sensing electrode, or automatically resetting a programmed sensing electrode configuration, e.g., from Vtip-Vring to Vtip-Vcoil. In some embodiments, the automatic corrective action is performed iteratively and incrementally, and after each adjustment ICD 10 determines whether oversensing persists. The automatic corrective action taken by ICD 10 may be dependent on the type of oversensing detected. For instance, ICD 10 may take different corrective actions for oversensing caused by R-wave double counting as opposed to oversensing caused by T-wave oversensing or myopotential oversensing.

Upon adjusting one or more sensing parameters of ICD 10, microprocessor 224 determines whether ICD 10 will appropriately detect a true cardiac episode with the adjusted sensing parameters at step 576. In some embodiments, microprocessor 224 applies the adjusted sensing parameters to sense previously recorded cardiac episode data stored in memory within the ICD. The episode data is a previously recorded intracardial electrogram of a cardiac episode. Microprocessor 224 can, for example, deliver a waveform of the previously recorded intracardial electrogram to the inputs of sense amplifiers 200 and 204 via switch matrix 208. Microprocessor 224 applies the adjusted sensing parameters in order to determine whether, given the adjusted sensing parameters, ICD 10 is able to correctly detect true cardiac episodes. In this manner, the waveforms of the previously recorded intracardial electrogram are delivered within ICD 10, eliminating the need to induce a cardiac episode, such as VF, of the heart of the patient, which may be very painful for the patient.

When microprocessor 224 determines that the adjusted sensing parameters result in the inability of ICD 10 to detect true cardiac episodes, microprocessor 224 resets the sensing parameters to the original settings at step 577. For example, if the sensitivity of the sensing electrode was decreased such that ICD 10 no longer accurately detects true capture of the heart, microprocessor 224 may reset the sensitivity to the original value that caused oversensing. In this manner, IMD 10 errs on the side of delivering an unnecessary therapy as opposed to not delivering a necessary therapy.

A report of the oversensing and the suspected cause is generated at step 578 in the manner described previously, for a physician. In the case that the automatic corrective action sufficiently detects true cardiac episodes, the report may include the automatic corrective actions taken so that the physician is notified of the changes. Further, in the case that the adjusted parameters were reset to their original values, a corrective action may be recommended by ICD 10 that the physician performs to prevent future inappropriate arrhythmia detections and unneeded delivery of cardioversion or defibrillation therapies. In this manner, upon device interrogation, the physician will be made aware of the identified oversensing, its likely cause and any automated corrective actions taken and thus be able to make therapeutic decisions based on this information. Additionally or alternatively, a patient notification signal may be issued, advising the patient to seek medical attention. The report generated at step 575 may include any automatic corrective actions taken by the ICD 10 such that the physician is notified of such changes.

If oversensing is not identified at decision step 550 and an arrhythmia has been detected, programmed anti-arrhythmia therapies are delivered by the ICD 10 at step 580. EGM episode data may be stored as normally performed during ICD 10 operation upon an arrhythmia detection.

Figure 7:
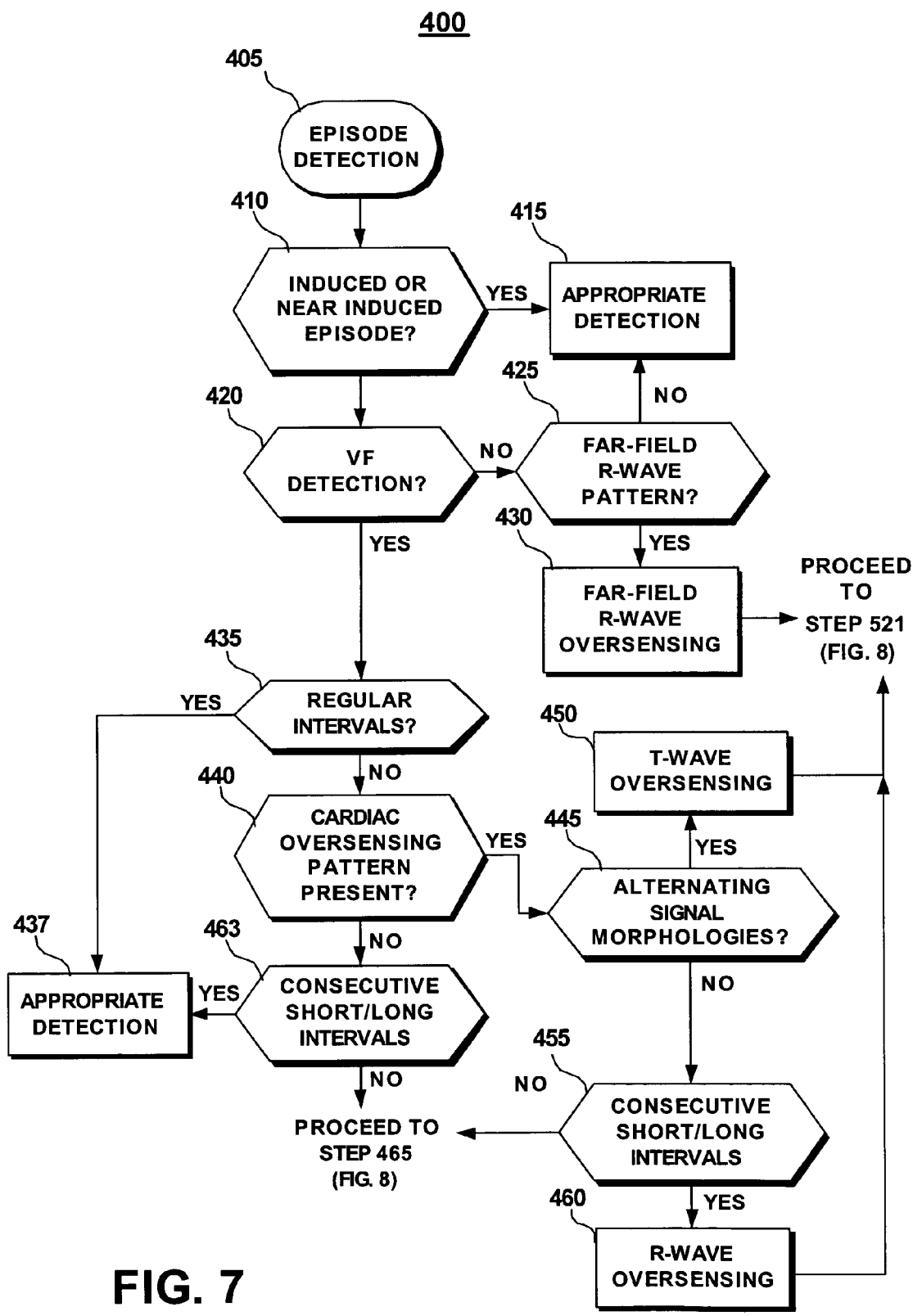
FIGS. 7 and 8 depict a flow chart summarizing a method that may be used in the embodiments of FIG. 5 or 6 for automatically identifying inappropriate arrhythmia detection due to oversensing.
Figure 8:
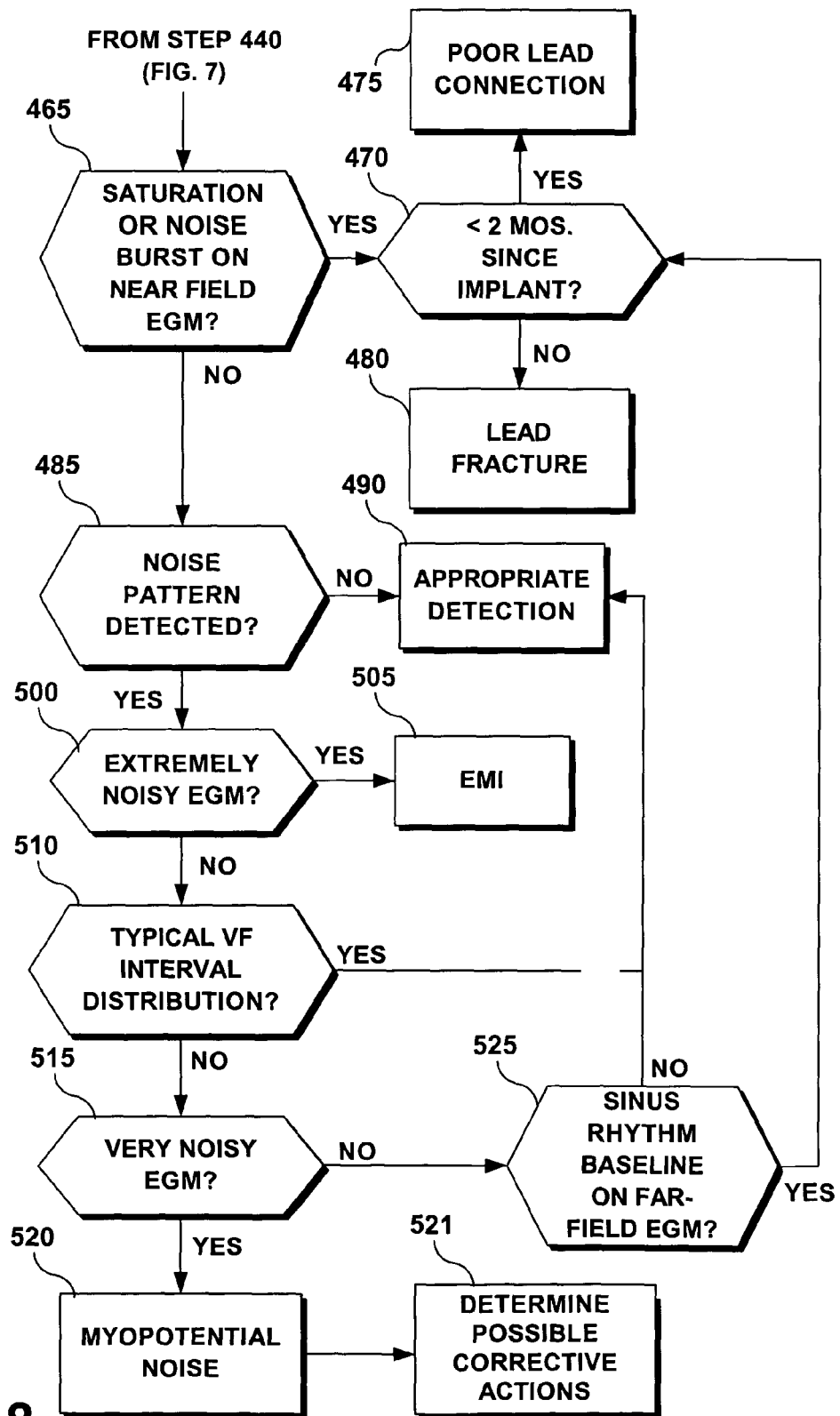

A preferred embodiment of a method for analyzing EGM data performed at step 400 in FIGS. 5 and 6 is summarized in the flow chart shown in FIGS. 7 and 8. The method 400 shown in FIGS. 7 and 8 is aimed at identifying inappropriate arrhythmia detections due to oversensing and determining the cause of the oversensing. Therefore, the method 400 is performed to analyze EGM episode data, associated with arrhythmia detection. However, it is recognized that the methods of FIGS. 7 and 8 can be adapted to analyze EGM data associated with triggering events of other monitoring algorithms. If the method 400 is performed offline, a stored EGM associated with an arrhythmia detection is loaded at step 405. During online analysis, an arrhythmia detection is recognized at step 405 and triggers the subsequent analysis.

The EGM episode data, including signal morphology, sensed and/or paced intervals, and sensed and/or paced event annotations, immediately prior to arrhythmia detection will be analyzed by the method 400. The data segment to be analyzed preferably includes on the order of 10 to 25 sensed intervals leading up to arrhythmia detection. The analysis preferably excludes EGM data immediately following a pacing pulse, for example 120 milliseconds of data following a pacing pulse, in order to eliminate pacing polarization artifacts from the data analysis. The analysis also preferably excludes the first 200 milliseconds of a stored EGM episode in order to exclude saturation of the EGM amplifier 210, which typically occurs when the EGM amplifier is first enabled.

At decision step 410, the analysis 400 determines if the arrhythmia has been intentionally induced during electrophysiological testing. Electrophysiological testing is generally performed to determine the susceptibility of a patient to arrhythmias and to aid in selecting programmable therapy options. An arrhythmia may be induced by methods known in the art, such as delivering a shock or pacing pulses coincidentally with the T-wave or delivering a 50-Hz burst. Any of these induction methods will be associated with annotated induction events stored with the EGM data. The annotated events may be used to automatically discriminate between induced arrhythmia episodes and spontaneous arrhythmia episodes. If an arrhythmia is detected at or near the time of an arrhythmia induction, the detection is classified as an appropriate detection at step 415, and the method 400 is terminated. When the method 400 is embodied in the ICD 10 for real-time episode analysis, the analysis can preferably be enabled or disabled by a programming command, allowing a physician to disable the method 400 during electrophysiological testing.

If a detected arrhythmia is not related to an induction, the method 400 determines if the detected arrhythmia is ventricular fibrillation (VF) as detected by the device in order to exclude ventricular tachycardia (VT) episodes at decision step 420. If VF is not detected, meaning the episode was detected as ventricular tachycardia (VT), the method 400 determines at decision step 425 if the interval pattern is representative of far-field R-wave sensing. Far-field R-wave sensing occurs when the ventricular R-wave is sensed by the atrial sense amplifier 204 resulting in a signal on P-out signal line 206. Intermittent oversensing of the far-field R-wave leads to inappropriate VT detection because the interval patterns are not representative of atrial fibrillation, atrial flutter or consistent far-field R-wave oversensing. A method for identifying the likelihood that events sensed in the atrium are in fact far-field R waves, rather than P waves, is described in the previously incorporated U.S. Pat. No. 5,545,186 issued to Olson et al. If an intermittent far-field R-wave pattern is present, the method 400 identifies the episode as an inappropriate arrhythmia detection due to far-field R-wave oversensing at step 430. As described above, ICD 10 may determine a recommended corrective action to reduce the likelihood of oversensing at step 521 (FIG. 8). Possible corrective actions for far-field R-wave oversensing include, for example, reprogramming an atrial sensitivity value to decrease the sensitivity of the atrial electrode, reconfiguring the electrode configuration or polarity of an atrial lead, or the like. In addition, in some embodiments, ICD 10 automatically performs the recommended corrective actions in accordance with the invention. If a far-field R-wave pattern is not present, oversensing is not identified. The EGM episode is identified as an appropriate arrhythmia detection at step 415, and the method 400 is complete.

If the arrhythmia is detected as VF at decision step 420, the method 400 evaluates the detected interval regularity at step 435. A VF detection may be a true VF episode, but it may also be ventricular tachycardia (VT) or supraventricular tachycardia detected as VF if the rate is high enough to fall into the VF detection zone. High rate VT is the most common arrhythmia that can be detected as VF. During a VT episode, the sensed intervals will be relatively regular compared to intervals associated with oversensing of cardiac events or noise. One method for evaluating the interval regularity in order to differentiate a VF detection due to a high rate VT from a VF detection due to oversensing is to calculate a sum of successive interval differences. For example, the difference between each consecutive pair of intervals for a given number of the most recent intervals leading up to VF detection may be summed. If the sum of these consecutive interval differences is less than a predetermined maximum, the intervals are considered regular. For example, a criterion for detecting interval regularity may require that the sum of 12 consecutive interval differences be less than 150 milliseconds. If interval regularity is detected, the method 400 identifies the episode as an appropriate arrhythmia detection at step 437, and the EGM analysis is complete.

If the intervals are determined to be irregular at decision step 435, the method 400 continues to decision step 440 to determine if an interval pattern indicative of cardiac oversensing is present. As shown previously in FIG. 1, cardiac oversensing in the ventricle can include oversensing of T-waves or R-waves. In these cases of cardiac oversensing, one extra ventricular sensed event occurs during each cardiac cycle.

Figure 9:
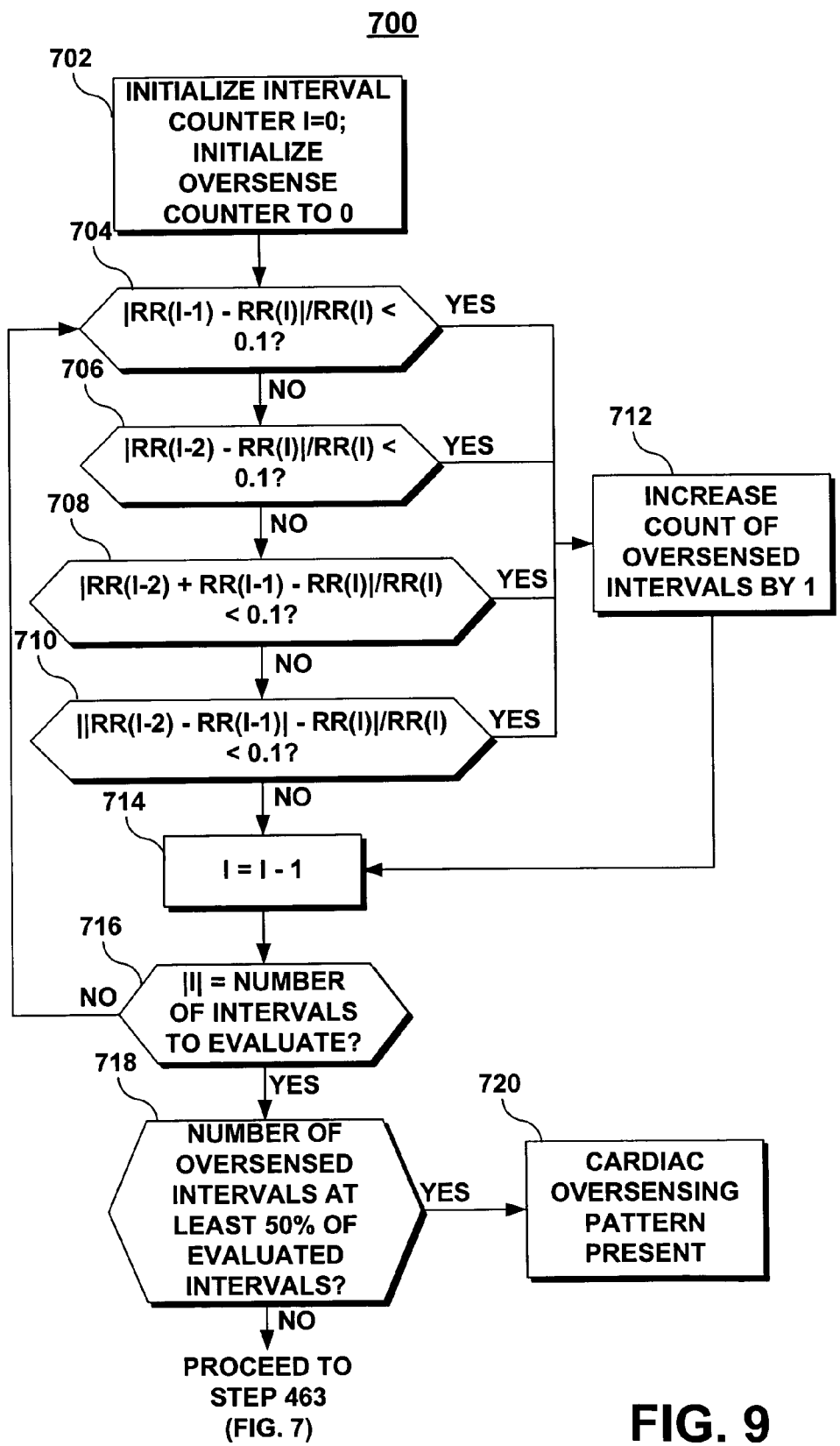
FIG. 9 is a flow chart illustrating a method for detecting a cardiac oversensing interval pattern that may be used in one embodiment of the method shown in FIGS. 7 and 8.

One method for recognizing a pattern indicative of cardiac oversensing is summarized by the flow chart shown in FIG. 9. The method 700 compares a sensed R-R interval to previous R-R intervals to determine if the R-R interval is a true R-R interval or, together with a previous interval, forms a true R-R interval. The term "R-R interval" herein refers to the interval between two events sensed in the ventricle. These events may or may not be real R-waves, therefore a sensed R-R interval may be an interval between various oversensed events and R-waves. If one intervening oversensed event has caused the true R-R interval to be divided into two intervals then the sum of two intervals will equal the true R-R interval. By examining for interval patterns that are representative of one oversensed event occurring per cardiac cycle, cardiac oversensing can be discriminated from oversensing due to other, non-cardiac sources, such as EMI or a lead fracture, which would typically occur more frequently during a cardiac cycle.

The method 700 for recognizing a cardiac oversensing pattern begins at step 702 by initializing an interval counter (I) to a value of 0. This interval counter will count the number of intervals included in the analysis performed by method 700 beginning with the interval upon which the VF detection was made, referred to as RR(0), and including a given number of intervals prior to the VF detection, preferably on the order of 12 intervals. At step 702, a second counter used for counting the number of intervals identified as being associated with a cardiac oversensed event is also initialized to a value of zero. In a preferred embodiment, patterns of cardiac oversensing are recognized by comparing a sensed R-R interval to each of: 1) the previous R-R interval, 2) the R-R interval prior to the previous interval, 3) the sum of the two previous intervals, and 4) the absolute value of the difference of the two previous intervals. If cardiac oversensing is occurring, at least one of these four comparisons will match.

These comparisons are made at decision steps 704, 706, 708 and 710. At step 704, the interval occurring at VF detection, RR(0), is compared to the next previous interval RR(−1). If RR(−1) is within 10% of RR(0), these intervals are approximately equal, and an oversensing interval counter is increased to one at step 712. To allow for small fluctuations that can normally occur in cardiac sensed intervals, the comparisons made at steps 704, 706, 708, and 710 are calculated as a ratio of the interval difference to the interval being analyzed, RR(I), and that ratio is compared to a value close to zero, such as 0.1, which is selected by a the physician, in order to allow for a normal 10% variation in detected cardiac intervals.

At step 706, the difference between R(0) and the interval prior to the previous interval, referred to as RR(−2), is calculated as a ratio to RR(0) and compared to a value of 0.1. At step 708, the sum of the two previous intervals RR(−1) and RR(−2) is compared to RR(0), and at step 710, the difference of the two previous intervals RR(−1) and RR(−2) is compared to RR(0). If any of these comparisons at steps 704 through 710 are satisfied, the oversense counter is increased by one at step 712.

The comparisons made at steps 704 through 710 may also be represented by the following equation:

$$\text{MIN}\{|(RR_{i-1}-RR_i)/RR_i|, |(RR_{i-2}-RR_i)/RR_i|, |((RR_{i-1}+RR_{i-2})-RR_i)/RR_i|, |(|RR_{i-1}-RR_{i-2}|-RR_i)/RR_i|\} < A \quad (1)$$

wherein $RR_i$ is a given R-R interval starting with the first R-R interval sensed at arrhythmia detection, $RR_{i-1}$ is the R-R interval preceding $RR_i$, $RR_{i-2}$ is the R-R interval preceding $RR_{i-1}$, and A is the predetermined value representing an expected variation in cardiac cycles, such as 0.1. If the minimum absolute value of the four comparisons shown in equation (1) is less than A, then two of the intervals $RR_i$, $RR_{i-1}$, or $RR_{i-2}$ may be associated with a cardiac oversensed event.

If none of these comparisons are satisfied at steps 704 through 710, then the interval counter I is decreased by one at step 714, and its absolute value is compared to the number of intervals to evaluate at step 716. If the number of intervals to evaluate has not been reached, the method 700 returns to step 704 and repeats the four comparisons at steps 704 through 710 for the next previous interval prior to VF detection. This process (steps 704 through 716) continues to step back through the sensed R-R intervals, starting from the R-R interval at detection, until the desired number of intervals prior to VF detection has been analyzed.

After the desired number of intervals has been reached at step 716, the value of the oversense interval counter is compared to the number of intervals evaluated at decision step 718. Criteria for recognizing a cardiac oversensing pattern may be predefined, for example requiring that a given percentage of the intervals prior to the detection event, for example 50%, satisfy the comparison of Equation (1) above or steps 704 through 710.

In TABLE I, a sample sequence of sensed interval lengths is listed in the first column with the corresponding minimum value determined from Equation (1) listed in the second column. The value of the oversensed interval count as Equation (1) is applied to each interval is shown in the third column of TABLE I. For this example, 11 of 12 intervals satisfy the Equation (1) indicating a pattern of cardiac oversensing.

TABLE I

| INTERVAL LENGTH | MINIMUM FROM EQUATION (1) | OVERSENSE COUNTER VALUE |
|---|---|---|
| 250 | 0.08 | 1 |
| 270 | 0.0 | 2 |
| 270 | 0.0 | 3 |
| 280 | 0.04 | 4 |
| 270 | 0.0 | 5 |
| 270 | 0.0 | 6 |
| 280 | 0.04 | 7 |
| 270 | 0.0 | 8 |
| 520 | 0.04 | 9 |
| 270 | 0.0 | 10 |
| 270 | 1.0 | 10 |
| 540 | 0.02 | 11 |
| 530 | — | — |
| 540 | — | — |

If the cardiac oversensing criteria is not met at decision step 718, then the method 400 proceeds to step 463 (FIG. 7) to continue to search for other causes of oversensing that may lead to an inappropriate arrhythmia detection. If the cardiac oversensing criteria is met at decision step 718, then a cardiac oversensing pattern is present as concluded at step 720. Additional analysis of the stored EGM is preferably performed by method 400 (FIG. 7) in order to identify the specific type of oversensing, e.g. T-wave oversensing. Additional verification is needed because the oversensing criteria described above in conjunction with FIG. 9 could also be satisfied if regular intervals, for example associated with ventricular tachycardia, or sinus tachycardia, are occurring.

Therefore, to verify that the arrhythmia detection is due to T-wave oversensing and not an appropriate VF detection, the method 400 of FIG. 7 next compares consecutively sensed signal morphologies at decision step 445. If alternating morphologies are occurring, T-wave oversensing is diagnosed as the cause of the VF detection at step 450, and the episode is identified as an inappropriate detection. ICD 10 determines a recommended corrective action to reduce the likelihood of oversensing at step 521 (FIG. 8). Possible corrective actions for T-wave oversensing include, for example, increasing a sensitivity value of a sensing electrode to decrease the sensitivity, reconfiguring the electrode configuration from tip-to-ring (true bipolar) to tip-to-coil (integrated bipolar), increasing a decay constant of the sensing electrode, or increasing the maximum auto-adjusting sensitivity threshold. For instance, ICD 10 may determine the appropriate corrective action to be increasing the decay constant of the sensing electrode from 450 milliseconds to 500 milliseconds. In addition, ICD 10 may automatically perform the recommended corrective actions dynamically in accordance with the invention.

Figure 10:
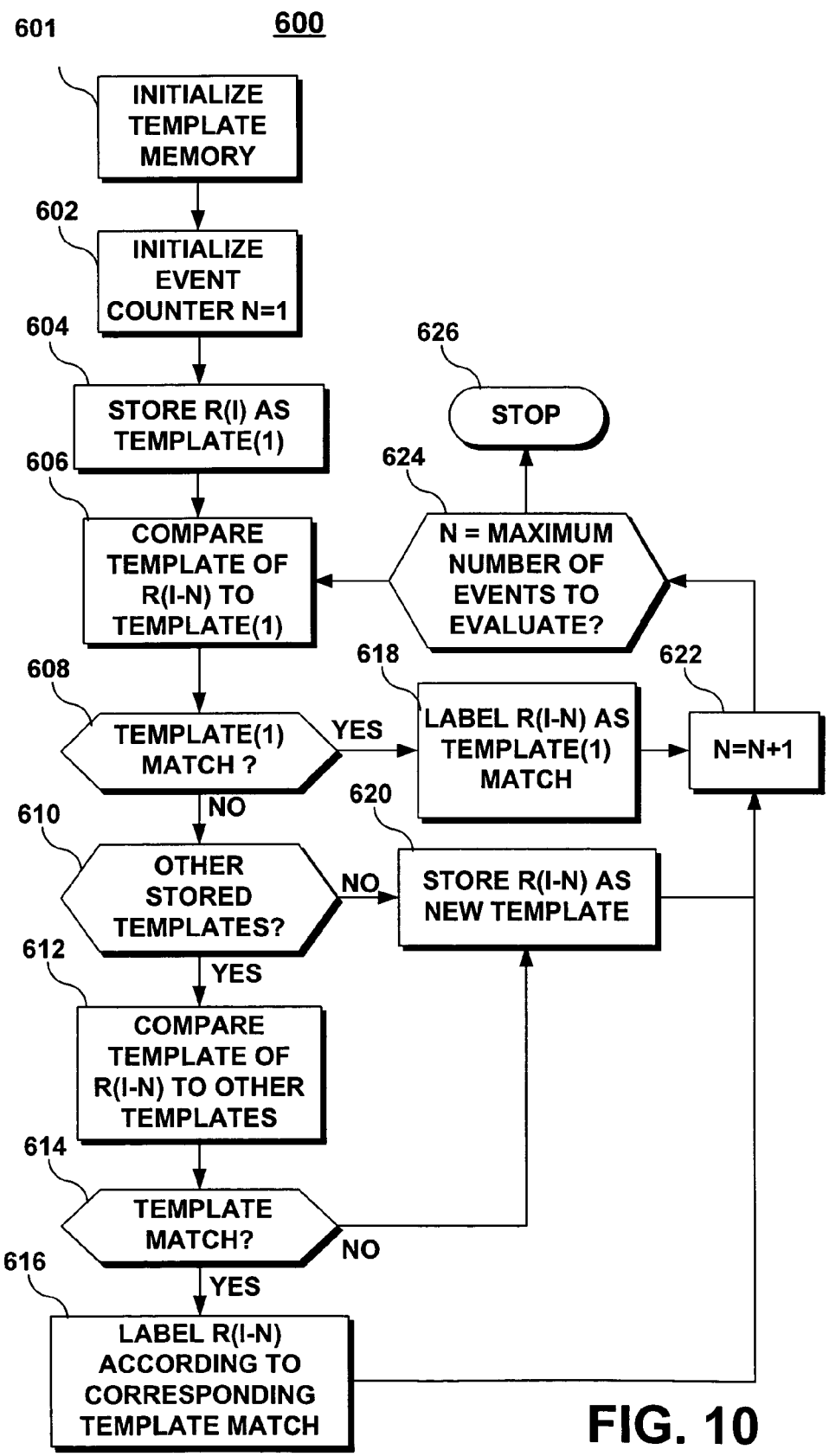
FIG. 10 is a flow chart illustrating a method for identifying alternating signal morphologies that may be used in one embodiment of the method shown in FIGS. 7 and 8 for identifying the occurrence of T-wave oversensing.

One method for performing the morphology analysis at step 445 is illustrated by the flow chart shown in FIG. 10. At step 601, designated areas of memory are initialized for storing morphology templates. At step 602, a counter for counting a desired number of sensed events that will be analyzed is initialized to a value of 1. The morphology of the sensed event occurring at VF detection, referred to as R(I), is stored as a first template, TEMPLATE(1), at step 604. The morphology of the sensed event prior to R(I), referred to as R(I−1), is compared to the stored template, TEMPLATE(1), at step 606.

If the morphology of R(I−1) approximately equals the TEMPLATE(1), as determined at decision step 608, then R(I−1) is labeled as a TEMPLATE(1) match at step 618. A template match indicates that R(I−1) is the same type of event as R(I). If the morphology of R(I−1) is different than TEMPLATE(1), it is stored as a second template, TEMPLATE(2), at step 620. A template match may be determined by calculating a correlation coefficient based on a point-by-point comparison of a sampled signal and a stored template. Calculation of a correlation coefficient may be performed as generally described in U.S. Pat. No. 5,193,550 issued to Duffin, incorporated herein by reference in its entirety.

At step 622, the counter N is increased by 1, and at step 624 the absolute value of the counter N is compared to the desired number of sensed events to be evaluated. If the desired number has been reached, preferably on the order of 24 events, then the morphology analysis is terminated at step 626. Otherwise, the morphology analysis continues by returning to step 606 to compare the next previous template, R(I−N) to TEMPLATE(1) at step 608. If the morphology of R(I−N) does not match TEMPLATE(1), the method 600 determines if any other morphology templates have been stored at decision step 610. If not, a new template is stored at step 620 with a template label.

Each time an event is found to be of a new morphology, in that it does not match a stored template, it is stored as a new template in one of the unoccupied, designated areas of memory. As new templates are stored, they may be labeled by consecutive numbers such that sensed events matching a given template may be labeled accordingly. If other stored templates do exist, as determined at decision step 610, the morphology of R(I−N) is compared to the other stored templates at step 612. If R(I−N) matches any of the stored templates, as determined at decision step 614, the sensed event R(I−N) is labeled according to the matching template at step 616.

After completing the morphology analysis 600, the method 400 of FIG. 7 can determine at decision step 445 if alternating signal morphologies are occurring that would be evidence of T-wave oversensing. For example, criteria for detecting alternating signal morphologies may require that alternating morphologies occur during at least one sequence of six consecutive events or during two sequences of five consecutive events. If so, the cardiac oversensing pattern detected at step 440 and the alternating signal morphologies detected at step 445 indicate that the detected arrhythmia is inappropriate due to T-wave oversensing as concluded at step 450. As described above, one such recommended or automatic corrective action could be to reprogram the ventricular sensitivity.

Figure 1:
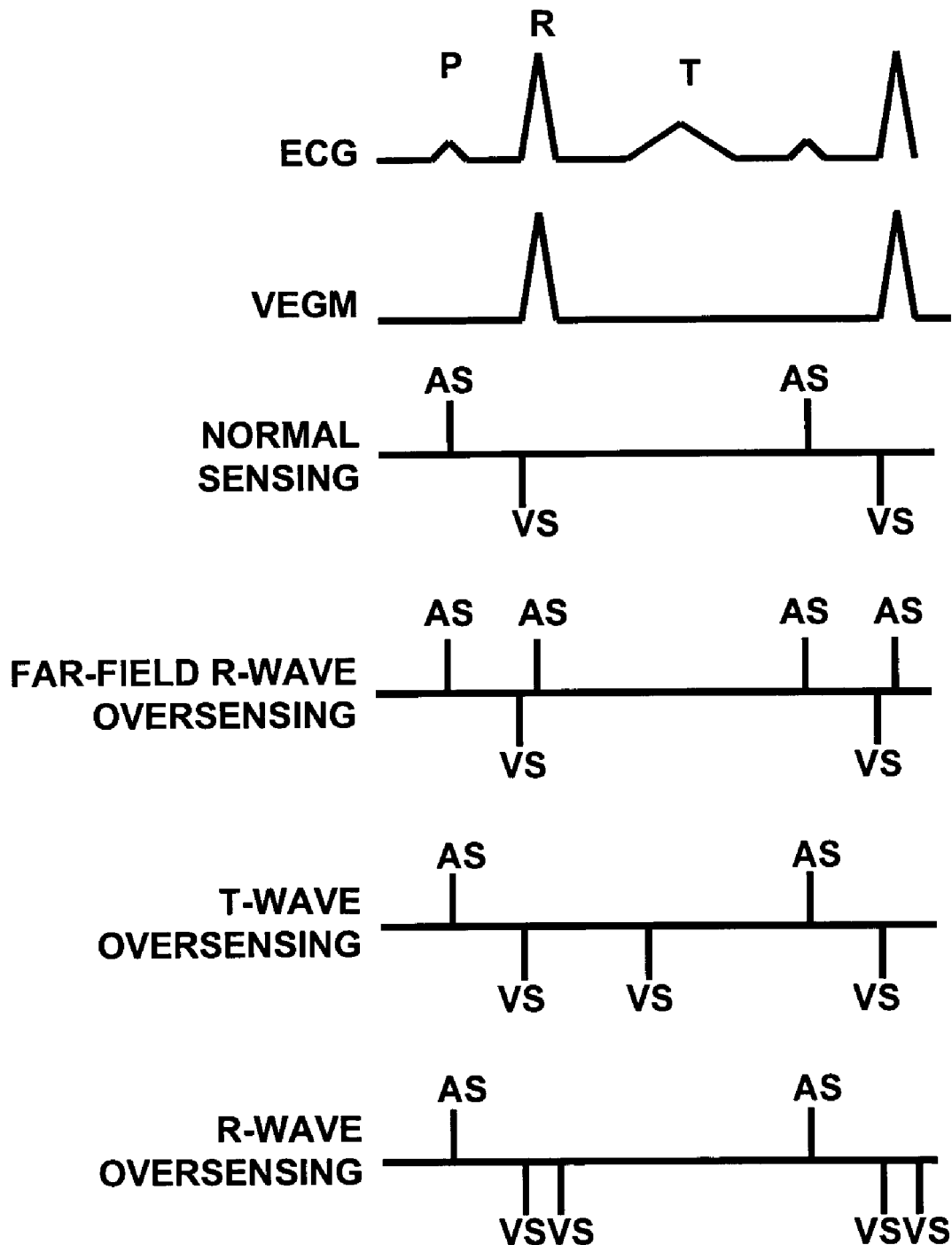
FIG. 1 is an illustration of a normal ECG signal, a corresponding ventricular EGM signal, and corresponding illustrations of sensed events occurring during normal sensing, far-field R-wave oversensing, T-wave oversensing, and R-wave oversensing.

If the signal morphologies are not alternating at step 445, the method 400 determines if short intervals are consecutive with long intervals at step 455. As illustrated in FIG. 1, alternating short and long intervals evidences R-wave oversensing (also referred to as R-wave double counting), as diagnosed at step 460. At decision step 455, a predetermined criteria for detecting the presence of short and long intervals indicative of R-wave oversensing may be used. R-wave oversensing will typically result in an interval of less than 160 milliseconds followed by an interval greater than 200 milliseconds in a repetitive manner. Therefore, criteria for recognizing a short-long interval pattern as evidence of R-wave oversensing may require, for example, at least four interval pairs comprising consecutive short and long intervals occurring within the 16 intervals prior to the arrhythmia detection, wherein the short interval is less than 160 milliseconds and the long interval is greater than 200 milliseconds. ICD 10 determines a recommended corrective action to reduce the likelihood of oversensing at step 521 (FIG. 8). Possible corrective actions for R-wave oversensing include, for example, increasing a sensitivity value of a sensing electrode to decrease the sensitivity, reconfiguring the sensing electrode configuration from tip-to-ring (true bipolar) to tip-to-coil (integrated bipolar), or increasing a blanking period of the sensing electrode. For instance, ICD 10 may determine the appropriate corrective action to be increasing the blanking period of the sensing electrode from 120 milliseconds to 140 milliseconds. In addition, ICD 10 may automatically perform the recommended corrective actions dynamically in accordance with the invention.

If the presence of short and long intervals is not detected at step 455, cardiac oversensing is not verified, and the method 400 proceeds to step 465 (FIG. 8) to evaluate the EGM signals for the presence of noise. If the cardiac oversensing criteria was not met initially at decision step 440, the method 400 proceeds to step 463 to verify that an irregular pattern of consecutive short and long intervals does not exist.

Cardiac oversensing may still be occurring but in an irregular pattern if the heart rhythm is an irregular tachycardia. Therefore, consecutive short and long intervals of varying lengths can exist if cardiac oversensing is occurring during irregular ventricular tachycardia. The irregular ventricular tachycardia may be detected as VF due to cardiac oversensing, such as R-wave oversensing, but in this case an arrhythmia does exist making the arrhythmia detection appropriate. If consecutive short and long intervals are recognized at decision step 463, the arrhythmia detection is identified as an appropriate detection at step 437, otherwise the method 400 proceeds to step 465 to evaluate the EGM for the presence of noise.

If one or more near-field EGM signals has been stored, they are examined at step 465 for saturation or bursts of noise. Saturation or bursts of noise on the near-field EGM are evidence of a lead fracture or poor lead connection, as previously shown in FIG. 2C. Saturation may be detected as a predetermined minimum number of consecutive digitized samples equal to the maximum analog-to-digital conversion unit. The analog EGM signal is converted to a digitized signal by sampling the analog signal at a given sampling frequency, for example every 8 milliseconds. The analog voltage amplitude of each sampled point is converted to a digital unit, referred to as an "A/D unit," using an analog-to-digital conversion factor. One A/D unit may equal 8 mV, for example, with a maximum A/D unit amplitude of 127 units. Therefore, in one embodiment, saturation of the near-field EGM may be detected when at least five consecutively sampled points equal the maximum A/D unit amplitude of 127 units.

Figure 11:
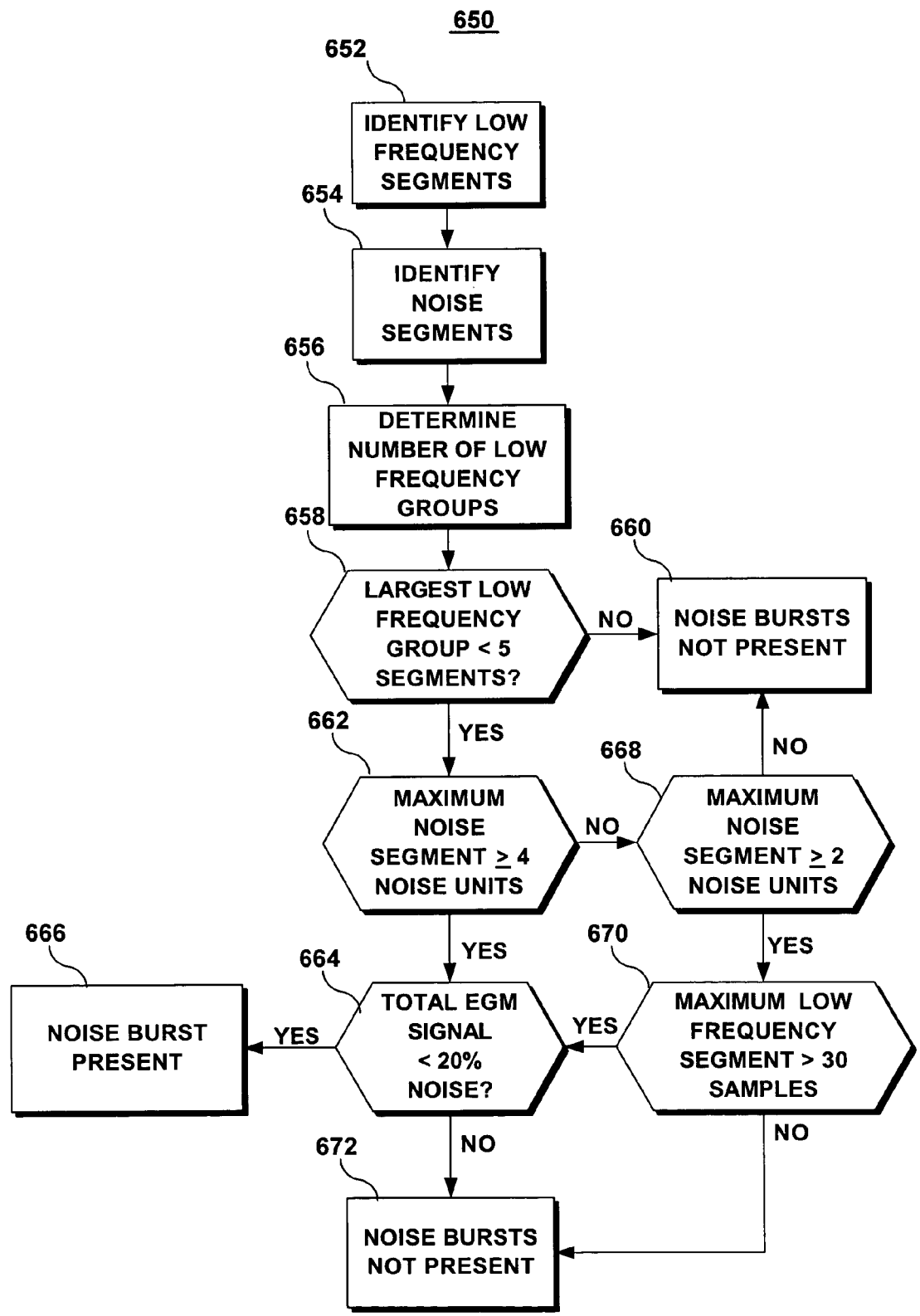
FIG. 11 is a flow chart illustrating a method for detecting noise bursts that may be used in one embodiment of the method shown in FIGS. 7 and 8 for diagnosing a lead fracture or poor lead connection.

If a lead fracture has occurred or the lead is poorly connected, intermittent bursts of noise will interrupt periods of low frequency on the near-field EGM signal. A method 650 for recognizing noise bursts that may be performed at decision step 465 is shown by the flow chart of FIG. 11. In order to recognize noise bursts, low frequency signal segments and noise segments must be discriminated in the EGM signal. At step 652, the low frequency EGM segments are identified. A low frequency signal sample may be defined as one in which the change in amplitude compared to the previous sample is less than a given maximum number of A/D units, for example less than 5 A/D units. Consecutive low frequency signal samples form a low frequency signal segment. For example, a sequence of digitized sample point amplitudes is listed in TABLE II below.

TABLE II

| 100 | 25  | 0 | 4 | 3 | 2 | 0 | 0 | 5 | 10 | 50 |
|-----|-----|---|---|---|---|---|---|---|----|----|
| −30 | −40 |   |   |   |   |   |   |   |    |    |

A change in amplitude of less than 5 A/D units is recognized between the third and fourth samples, 0 and 4. These samples are at the start of a low frequency segment totaling six samples including the samples having amplitudes of: 0, 4, 3, 2, 0, and 0. All other samples in the above sequence have a change in A/D amplitude of 5 units or more.

At step 654, noise segments of the EGM are identified. A unit of noise may be defined as two consecutive signal samples that vary in amplitude by more than a predetermined number of A/D units, for example 3 A/D units, and represent a change in amplitude direction. For example, in the sequence of TABLE II, the only noise unit exists between the points 50 and −30. The amplitude change between 50 and −30 represents a change in direction, from positive going from the previous sample 10 to 50, to negative going from 50 to −30, and a change in amplitude of greater than 3 A/D units.

A noise burst comprises a group of low frequency signal segments with short, intervening noise segments. Therefore, at step 656, low frequency groups are identified and counted. A low frequency group may be identified as two or more low frequency segments that are at least 20 sample points in length with a difference in length of 10 sample points or less. For example, the number of sampled points in each of a number of detected low frequency segments is listed in TABLE III below.

TABLE III

| 6 | 10 | 12 | 14 | 20 | 21 | 23 | 23 | 26 | 30 | 32 | 34 |
|---|----|----|----|----|----|----|----|----|----|----|----|

The sample sequence in TABLE III includes a group of six low frequency segments having 20, 21, 23, 23, 26, and 30 sample points each. The segments having less than 20 sample points are not considered part of a group according to the above defined criteria. The segments of 32 and 34 sample points each are more than 10 sample points greater than the segments of 20 and 21 sample points and are therefore not included in the group. Another group of low frequency segments includes the five segments of 23, 23, 26, 30, and 32 sample points. Each of these segments are greater than 20 sample points in length and their lengths are within 10 sample points of each other. In this example, the largest group of the low frequency segments is a group of six low frequency segments.

After identifying the low frequency segments and the noise segments, numerous criteria may be set forth for identifying a noise burst based on the number of low frequency groups, the length of low frequency segments, the length of noise segments, and/or the overall percentage of noise present in the EGM signal. The percentage of noise in the EGM signal may be determined as the total number of noise units divided by the total number of EGM samples multiplied by 100 percent. A set of criteria for identifying noise bursts used by method 650 of FIG. 11 has a first criterion limiting the largest group of low frequency segments to less than five segments, as determined at decision step 658. If the largest low frequency group has five or more segments, a conclusion is made at step 660 that noise bursts are not present on the EGM signal. If the largest low frequency group is less than five segments and the maximum noise segment during the entire EGM segment analyzed is four or more noise units in length as determined at decision step 662, and less than 20% of the total EGM signal is identified as noise at decision step 664, then a noise burst is present as concluded at step 666.

Alternatively, if the largest low frequency group is less than 5 segments (decision step 658), the maximum noise segment is at least two noise units as determined at decision step 668, and the maximum low frequency segment in the entire EGM segment analyzed is greater than 30 sample points as determined at decision step 670 with less than 20% of the EGM signal identified as noise at decision step 664, then a noise burst is present as concluded at step 666. If these criteria are not met at steps 658, 662, 664, 668 and 670, then the conclusion is made that noise bursts are not present at step 672.

If either saturation or a noise burst is found in a near-field EGM at decision step 465 (FIG. 7), then a lead fracture or poor lead connection is likely. If the lead carrying the sensing electrodes has been implanted for less than two months, as determined at step 470, the noise is likely due to poor connection of the lead to the implanted device. The time that an ICD has been implanted may be known, for example, by a time-stamp that is made when VF detection is first programmed to "on." This information is made available when stored EGM data is saved to a diskette in commercially available devices, for example in the Model 7275 GEM® III Dual Chamber Implantable Cardioverter Defibrillator available from Medtronic, Inc., Minneapolis, Minn. If the implant time is known to be less than two months, a diagnosis of oversensing due to poor lead connection is made at step 475, and the episode is identified as an inappropriate arrhythmia detection. A recommended corrective action could be to tighten the set screws on the connector block of the ICD 10.

If the lead has been implanted for more than two months, the intermittent noise bursts and/or signal saturation are likely due to a lead fracture, resulting in an inappropriate arrhythmia detection. This diagnosis is made at step 480. Further investigation through x-ray or invasive procedures may need to be performed to verify a lead fracture and, if found, repair or replace the lead.

If a near-field EGM has not been stored or if no saturation or noise bursts are present on a near-field EGM, as determined at decision step 465, the method 400 proceeds to step 485 to evaluate both the near-field and far-field EGM signals for noise, with priority given to the near-field EGM signal if it has been stored. At decision step 485, the method 400 looks for an interval pattern evidencing noise. Typically, very short R-R intervals will be sensed in the presence of noise. Therefore one criteria for detecting a noise interval pattern at decision step 485 it to detect at least two R-R intervals of less than 160 milliseconds out of the last 18 sensed R-R intervals. If a noise pattern is not present, the method 400 concludes at step 490 by classifying the arrhythmia detection as appropriate.

If a noise pattern is present, the method 400 proceeds to evaluate the near-field and/or far-field EGM to determine the type of noise present. Saturation or noise bursts associated with a lead fracture or poor lead connection are not observed on a far-field EGM signal. Therefore, the method 400 first analyzes the EGM to exclude other forms of noise that may cause an inappropriate arrhythmia detection, such as electromagnetic interference or other myopotentials.

At step 500, the near-field and/or far-field EGM signal is analyzed to determine what percentage of the signal is noise. An extremely noisy EGM episode, as can occur with electromagnetic interference, may be defined as an episode containing greater than a predefined percentage of noise units, for example greater than 60% of the EGM signal samples are identified as noise units. If the EGM signal is found to be extremely noisy at decision step 500, the detected arrhythmia is identified as inappropriate due to electromagnetic interference (EMI) at step 505. Electromagnetic interference is typically present as high-frequency, continuous noise, producing an extremely noisy (greater than 60% noise) EGM signal as previously illustrated in FIG. 2A.

If the EGM signal is not found to be extremely noisy at decision step 500, the sensed R-R interval distribution is examined at step 510 to determine if the intervals represent a typical VF interval distribution. An average R-R cycle length sensed during VF is typically around 220 milliseconds. If sensed R-R cycle lengths are much shorter or much longer than a typical VF cycle length, noise is likely to be present. At decision step 510, the method 400 may determine if any R-R cycle lengths are less than a predetermined minimum VF cycle length or greater than a predetermined maximum VF cycle length. These minimum and maximum cycle lengths represent the range of an expected VF cycle length distribution. A criterion for detecting a non-VF cycle length distribution at decision step 510, therefore, may require a given percentage, for example 50%, of the R-R intervals to be outside the typical VF distribution. In one embodiment, at least 6 of the last 12 R-R intervals must be less than 200 milliseconds or greater than 300 milliseconds with at least one of these intervals being greater than 300 milliseconds in order to detect a non-VF cycle length distribution. If a typical VF interval distribution is found at decision step 510, then the arrhythmia detection is identified as an appropriate detection at step 490. If a non-VF distribution is found, the method 400 continues to evaluate the EGM signal for noise associated with non-cardiac myopotentials.

Figure 2A:
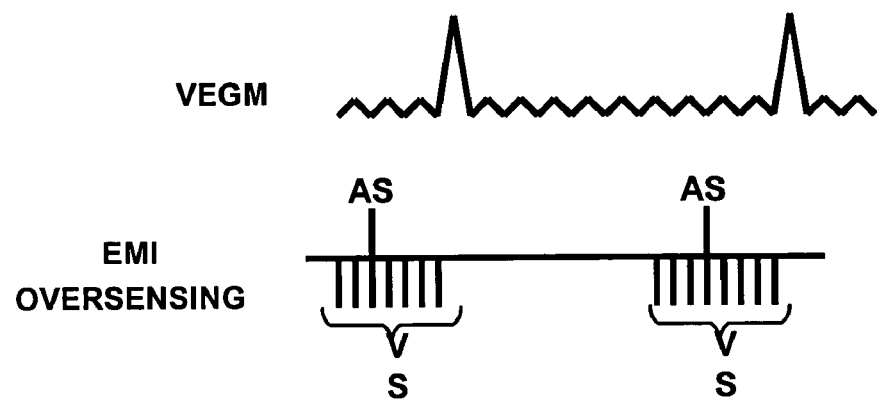
FIG. 2A is an illustration of a ventricular EGM signal with noise due to electromagnetic interference (EMI) and a corresponding example of EMI oversensing.
Figure 2B:
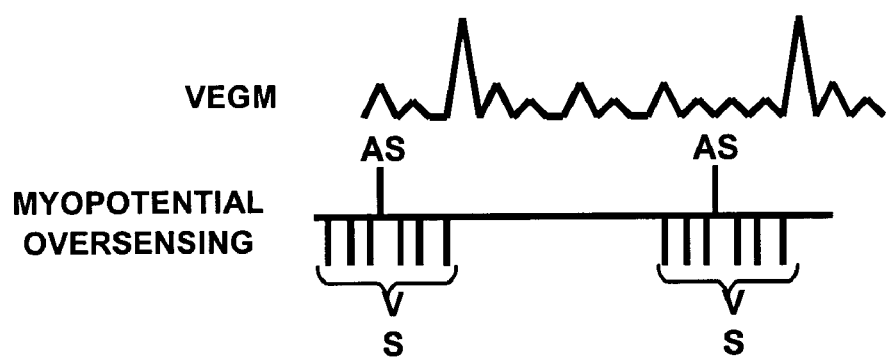
FIG. 2B is an illustration of a ventricular EGM signal with myopotential noise and a corresponding example of myopotential oversensing.
Figure 2C:
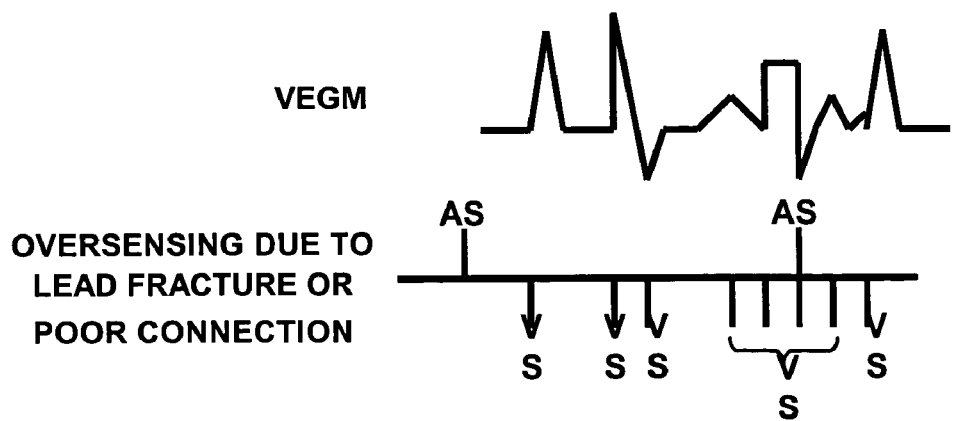
FIG. 2C is an illustration of a ventricular EGM signal with noise due to a lead fracture or poor lead connection and a corresponding example of oversensing.

Oversensing of myopotential noise is typically intermittent and of lower frequency than EMI oversensing, as previously shown in FIGS. 2A and 2B. Myopotential noise may produce a very noisy EGM signal comprising, for example, greater than 20% noise units but less than 60% noise units. If the EGM signal is determined to be very noisy at decision step 515, an inappropriate arrhythmia detection due to myopotential noise is diagnosed at step 520. ICD 10 may determine a recommended corrective action to reduce the likelihood of oversensing at step 521. Possible corrective actions for oversensing caused by a non-cardiac origin, e.g., myopotentials or EMI, include increasing a sensitivity value of a sensing electrode to decrease the sensitivity, reconfiguring the electrode configuration from tip-to-ring (true bipolar) to tip-to-coil (integrated bipolar), increasing a decay constant of the electrode, or increasing the maximum auto-adjusting sensitivity threshold. For instance, ICD 10 may determine the appropriate corrective action to be increasing the sensitivity value of the electrode from 0.3 millivolts to 0.45 millivolts. In addition, ICD 10 may automatically perform the recommended corrective actions dynamically in accordance with the invention.

If the EGM is not found to be very noisy at step 515, the baseline of the far-field EGM is examined. If VF is actually occurring, the EGM signal will be at the baseline value for only very short sample segments. If an inappropriate detection has been made due to a lead fracture or poor lead connection, longer EGM baseline segments will be present during sinus rhythm. In addition, a higher amplitude event consistent with a normal R-wave will normally exist in contrast to the lower amplitude fibrillation waves. Therefore, at decision step 525, the method 400 examines the far-field EGM for relatively long periods of baseline with at least one relatively large amplitude event, both of which would not be present during real VF but would represent a possible lead fracture or poor connection.

A segment of baseline may be identified as a segment in which the sum of the absolute value of the amplitudes of consecutive sampled points is less than a predetermined number of A/D units, for example 5 A/D units. If, at step 525, at least one baseline segment exceeding 160 milliseconds in length is present in the far-field EGM with at least one sample point greater than 2.5 mV, the arrhythmia detection is identified as inappropriate. If the lead carrying the sensing electrodes has been implanted for less than two months (decision step 470), the inappropriate detection is diagnosed as oversensing of noise due to a lead fracture at step 480. If the lead has been implanted less than two months, a diagnosis of oversensing due to poor lead connection is made at step 475. If a relatively long baseline and higher amplitude sample cannot be identified at decision step 525, the arrhythmia detection is an appropriate detection (step 490).

Thus, the methods shown in FIGS. 5 through 11 provide automatic identification of oversensing. Moreover, the methods described above allow causes of oversensing, which may lead to inappropriate arrhythmia detection, to be specifically identified based on an analysis of sensed EGM interval patterns and signal morphologies. Numerous sources of oversensing, which can be both cardiac and non-cardiac in origin, are systematically identified or eliminated by the methods included in the present invention, providing a physician with a powerful and time-savings tool for trouble-shooting the problem of oversensing. More accurate sensing of the heart rhythm may be achieved by identifying and automatically correcting oversensing, thereby allowing appropriate stimulation therapies to be delivered only when needed.

Figure 12:
FIG. 12 is an exemplary cardiac electrogram illustrating T-wave oversensing as well as exemplary automatic corrective actions to reduce the likelihood of T-wave oversensing.

FIG. 12 is an exemplary cardiac electrogram illustrating T-wave oversensing as well as exemplary automatic corrective actions to reduce the likelihood of T-wave oversensing. Specifically, the example illustrated in FIG. 12 shows an exponential decay curve 800 that illustrates the sensitivity of a sensing electrode, such as a ventricular electrode, after application of a pacing pulse. In other words, the sensitivity of the sensing electrode changes as a function of decay curve 800. ICD 10 operates in accordance with the sensitivity, e.g., sensitivity as a function of exponential decay curve 800, of the sensing electrode for a plurality of cardiac cycles. T-wave oversensing occurs at the first T-wave because a sensitivity of the sensing electrode is below the potential of the T-wave. In accordance with the invention, however, ICD 10 automatically performs one or more corrective actions to reduce the likelihood of oversensing. As described above, the corrective actions are performed in a dynamic fashion.

One such corrective action is to increase a maximum auto-adjusting sensitivity threshold of the sensing electrode such that the sensitivity of the sensing electrode is above the potential of the T-wave, as illustrated by decay curve 802 at the second T-wave. For example, the maximum auto-adjusting sensitivity threshold may be increased from 75% of the R-wave potential to 95% of the R-wave potential. In other words, the exponential decay curve representing the sensitivity of the sensing electrode is shifted up such that it is above the T-wave potential.

Another automatic corrective action that may be performed by ICD 10 includes increasing a decay constant of the sensing electrode, as illustrated decay curve 804 at the third T-wave. For example, the decay constant may be increased from 450 milliseconds to 500 milliseconds in order to decrease the exponential decay of the sensing electrode, thus decreasing the sensitivity such that the T-wave potential is not detected. Although illustrated separately, IMD 10 may use both corrective actions simultaneously to reduce the likelihood of oversensing.

The illustrated automatic corrective actions are by no means the only automatic corrective actions that may be taken to reduce the likelihood of T-wave oversensing. Other automatic corrective actions include changing an electrode configuration of the sensing electrode form a tip-to-ring configuration (e.g., true bipolar configuration) to a tip-to-coil configuration (e.g., integrated bipolar configuration). Further, the sensitivity of the sensing electrode may be decreased, e.g., by increasing the sensitivity value of the sensing electrode. Although described in terms of T-wave oversensing, these automatic corrective actions may be applied to reduce the likelihood of other cardiac or non-cardiac oversensing, such as myopotential oversensing.

Figure 13:
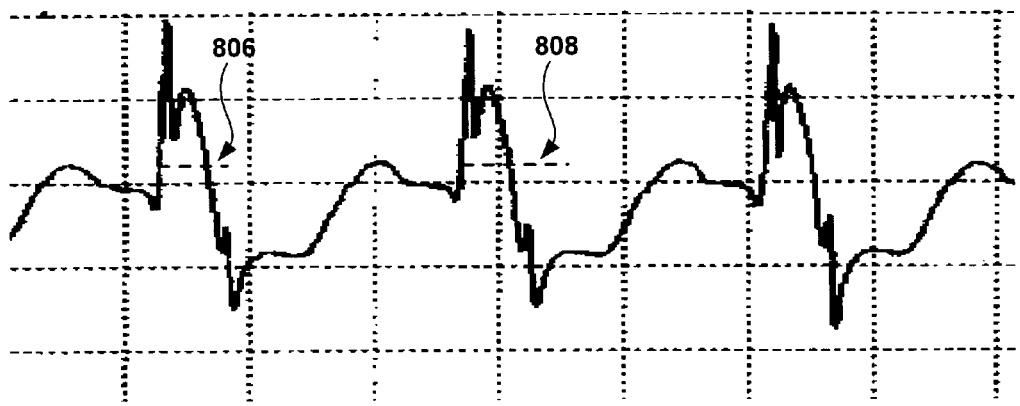
FIG. 13 is an exemplary cardiac electrogram illustrating R-wave oversensing as well as exemplary automatic corrective actions to reduce the likelihood of R-wave oversensing.

FIG. 13 is an exemplary cardiac electrogram illustrating R-wave oversensing (i.e., R-wave double counting) as well as exemplary automatic corrective actions to reduce the likelihood of R-wave oversensing. Specifically, the example illustrated in FIG. 13 shows a blanking period 806 representative of a period of time when a sensing electrode, such as a ventricular electrode, is shut off after application of a pacing pulse. R-wave oversensing occurs at the first R-wave because the blanking period of the sensing electrode ends before the R-wave potential is below a sensitivity of the sensing electrode. R-wave oversensing can occur, for example, when an R-wave complex is widened due to conditions such as bundle branch block or wide complex ventricular tachycardia. In accordance with the invention, however, ICD 10 automatically performs one or more corrective actions to reduce the likelihood of oversensing.

One such corrective action may be to increase the blanking period such that it covers the entire R-wave complex, as illustrated by blanking period 808. For example, the blanking period may be increased from 120 milliseconds to 140 milliseconds for a patient who experiences a widened R-wave complex due to bundle branch block.

The illustrated automatic corrective action is by no means the only automatic corrective actions that may be taken to reduce the likelihood of R-wave oversensing or R-wave double counting. Other automatic corrective actions include changing an electrode configuration of the sensing electrode form a tip-to-ring configuration (e.g., true bipolar configuration) to a tip-to-coil configuration (e.g., integrated bipolar configuration). Further, the sensitivity of the sensing electrode may be decreased, e.g., by increasing the sensitivity value of the sensing electrode. Although described in terms of R-wave oversensing, these automatic corrective actions may be applied to reduce the likelihood of other cardiac or non-cardiac oversensing.

The detailed descriptions of the preferred embodiments provided herein yield a sensitive and specific method for analyzing EGM signals and sensed interval patterns to diagnose oversensing of cardiac or non-cardiac signals and automatically adjusting sensing parameters, electrode configurations, and the like to reduce the likelihood of reoccurrence of the oversensing. Numerous variations of the described embodiments are possible for practicing the invention. Therefore, the embodiments described herein should be considered exemplary, rather than limiting, with regard to the following claims. These and other embodiments are within the scope of the following claims.

The invention claimed is:
1. A method comprising:
operating an implanted medical device in accordance with sensing parameters for a plurality of cardiac cycles;
identifying oversensing by the implanted medical device by performing real-time electrogram (EGM) analysis;

automatically adjusting at least one of the sensing parameters of the implanted medical device in response to identifying the oversensing to invoked corrective action to avoid future oversensing;
without inducing a cardiac episode,
prospectively assessing whether the implanted medical device will appropriately detect a cardiac episode with the adjusted sensing parameters; and
resetting the sensing parameter to an original setting upon determining the implanted medical device will not appropriately detect the cardiac episode with the adjusted sensing parameters.

2. The method of claim 1, further comprising:
determining an origin of the oversensing; and
automatically adjusting at least one sensing parameter based on the origin of the oversensing.

3. The method of claim 2, wherein the origin of the oversensing includes one of cardiac origin and non-cardiac origin.

4. The method of claim 3, wherein the oversensing from a cardiac origin includes one of T-wave oversensing, R-wave double counting, far-field R-wave oversensing, and P-wave oversensing.

5. The method of claim 1, wherein automatically adjusting the sensing parameter includes automatically adjusting a programmed sensitivity of a sensing electrode.

6. The method of claim 1, wherein automatically adjusting the sensing parameter includes automatically adjusting a programmed threshold of a sensing electrode.

7. The method of claim 1, further comprising reporting the adjustments to the sensing parameters to a physician upon interrogation.

8. The method of claim 1, wherein identifying oversensing by an implanted medical device includes identifying oversensing using intracardiac electrograms.

9. The method of claim 1, wherein automatically adjusting the sensing parameter includes automatically adjusting an electrode configuration of a sensing electrode.

10. The method of claim 9, wherein automatically adjusting the electrode configuration includes adjusting the electrode configuration from a true bipolar sensing (tip-to-ring) configuration to an integrated bipolar sensing (tip-to-coil) configuration.

11. The method of claim 1, wherein automatically adjusting the sensing parameter includes automatically adjusting a programmed decay constant of a sensing electrode.

12. The method of claim 1, wherein automatically adjusting the sensing parameter includes automatically adjusting a programmed decay delay of a sensing electrode.

13. The method of claim 1, wherein automatically adjusting the sensing parameter includes automatically adjusting a programmed blanking period of a sensing electrode.

14. A computer-readable medium comprising instructions to cause a processor to:
operate an implanted medical device in accordance with sensing parameters for a plurality of cardiac cycles;
identify oversensing by the implanted medical device by performing real-time electrogram (EGM) analysis; and
automatically adjust at least one sensing parameter of the implanted medical device in response to identifying the oversensing;
without inducing a cardiac episode,
prospectively assess whether the implanted medical device will appropriately detect a cardiac episode with the adjusted sensing parameters; and,
reset the sensing parameter to an original setting upon determining the implanted medical device will not appropriately detect the cardiac episode with the adjusted sensing parameters.

15. The computer-readable medium of claim 14, further comprising instructions to cause the processor to:
determine an origin of the oversensing; and
automatically adjust the sensing parameter based on the origin of the oversensing.

16. The computer-readable medium of claim 14, wherein instructions to cause the processor to automatically adjust at least one sensing parameter of the implanted medical device includes instructions to cause the processor to automatically adjust at least one of a programmed sensitivity of a sensing electrode, a programmed threshold of a sensing electrode, a programmed decay constant of a sensing electrode, a programmed decay delay of a sensing electrode, a programmed blanking period of a sensing electrode, and an electrode configuration of a sensing electrode.

17. An implantable medical device comprising:
at least one sensing electrode to sense cardiac data from a heart of a patient in accordance with programmed sensing parameters for a plurality of cardiac cycles; and
a processor to identify oversensing by the implantable medical device based on the sensed cardiac data and automatically adjust at least one of the sensing parameter of the implantable medical device in response to identifying the oversensing;
wherein the processor prospectively assesses, without inducing a cardiac episode, whether the implantable medical device will appropriately detect a cardiac episode with the adjusted sensing parameter and resets the sensing parameter to an original setting upon determining the implantable medical device will not appropriately detect the cardiac episode with the adjusted sensing parameter.

18. The device of claim 17, wherein the processor determines an origin of the oversensing and automatically adjusts the sensing parameter based on the origin of the oversensing.

19. The device of claim 17, wherein the processor automatically adjusts a programmed sensitivity of the sensing electrode in response to identifying oversensing.

20. The device of claim 17, wherein the processor automatically adjusts a programmed threshold of the sensing electrode in response to identifying oversensing.

21. The device of claim 17, wherein the processor automatically adjusts a programmed decay constant of the sensing electrode in response to identifying oversensing.

22. The device of claim 17, wherein the processor automatically adjusts a programmed decay delay of the sensing electrode in response to identifying oversensing.

23. The device of claim 17, wherein the processor automatically adjusts a programmed blanking period of the sensing electrode in response to identifying oversensing.

24. The device of claim 17, wherein the processor automatically adjusts an electrode configuration of the sensing electrode in response to identifying oversensing.

25. The device of claim 24,
wherein the processor automatically adjusts the electrode configuration from a true bipolar sensing (tip-to-ring) configuration to an integrated bipolar sensing (tip-to-coil) configuration.

26. The device of claim 17, wherein the implantable medical device reports the adjustment to the sensing parameter to a physician upon interrogation.

27. The device of claim 17, wherein the processor identifies oversensing by an implantable medical device using intracardiac electrograms.

28. An implantable medical device comprising:
- means for operating an implantable medical device in accordance with sensing parameters for a plurality of cardiac cycles;
- means for identifying oversensing by the implantable medical device;
- means for automatically performing a corrective action to reduce the likelihood of oversensing automatically by adjusting at least one of the sensing parameters;
- means for prospectively assessing, without inducing a cardiac episode, whether the implanted medical device will appropriately detect a cardiac episode with the adjusted sensing parameters; and
- means for resetting the sensing parameter to an original setting upon determining the implanted medical device will not appropriately detect the cardiac episode with the adjusted sensing parameters.

29. The device of claim 28, further comprising a sensing electrode to sense cardiac data, wherein the adjusted sensing parameter may include one of a programmed sensitivity of the sensing electrode, a programmed threshold of the sensing electrode, a programmed decay constant of the sensing electrode, a programmed decay delay of the sensing electrode, a programmed blanking period of the sensing electrode, and an electrode configuration of the sensing electrode.

30. The device of claim 28, further comprising means for assessing whether the implanted medical device will appropriately detect a cardiac episode with the adjusted sensing parameter.

31. The device of claim 28, further comprising means for determining an origin of the oversensing, and wherein the means for performing automatically performs the corrective action based on the origin of the oversensing.

32. The device of claim 28, wherein means for automatically performing the corrective action includes means for adjusting at least one of the sensing parameters.

* * * * *